US012661627B2

(12) United States Patent
Georgi et al.

(10) Patent No.: US 12,661,627 B2
(45) Date of Patent: *Jun. 23, 2026

(54) BIODEGRADABLE POLYUREA/POLYURETHANE MICROCAPSULES

(71) Applicant: Symrise AG, Holzminden (DE)

(72) Inventors: Julian Alexander Georgi, Holzminden (DE); Britta Raabe, Münden (DE); Benjamin Rost, Bodenwerder (DE); Andreas Vogel, Stadtoldendorf (DE); Ralf Bertram, Holzminden (DE); Daniela Gregor, Bevern (DE); Christina Koepke, Holzminden (DE); Stefanie Bargsten, Steinheim (DE); Patrick Ott, Holzminden (DE)

(73) Assignee: Symrise AG, Holzminden (DE)

( * ) Notice: Subject to any disclaimer, the term of this patent is extended or adjusted under 35 U.S.C. 154(b) by 466 days.

This patent is subject to a terminal disclaimer.

(21) Appl. No.: 18/019,795

(22) PCT Filed: Aug. 6, 2020

(86) PCT No.: PCT/EP2020/072206
§ 371 (c)(1),
(2) Date: Feb. 3, 2023

(87) PCT Pub. No.: WO2022/028708
PCT Pub. Date: Feb. 10, 2022

(65) Prior Publication Data
US 2024/0293790 A1 Sep. 5, 2024

(51) Int. Cl.
| | |
|---|---|
| *B01J 13/14* | (2006.01) |
| *A01N 25/28* | (2006.01) |
| *A01P 7/04* | (2006.01) |
| *A01P 17/00* | (2006.01) |
| *A61K 8/04* | (2006.01) |
| *A61K 8/84* | (2006.01) |
| *A61K 8/87* | (2006.01) |
| *A61K 9/50* | (2006.01) |
| *A61Q 13/00* | (2006.01) |
| *A61Q 19/00* | (2006.01) |
| *B01J 13/16* | (2006.01) |
| *B01J 13/20* | (2006.01) |
| *C11D 3/00* | (2006.01) |
| *C11D 3/37* | (2006.01) |
| *C11D 3/50* | (2006.01) |
| *C11D 17/00* | (2006.01) |

(52) U.S. Cl.
CPC .............. *B01J 13/16* (2013.01); *A01N 25/28* (2013.01); *A01P 7/04* (2021.08); *A01P 17/00* (2021.08); *A61K 8/04* (2013.01); *A61K 8/84* (2013.01); *A61K 8/87* (2013.01); *A61K 9/5031* (2013.01); *A61Q 13/00* (2013.01); *A61Q 19/00* (2013.01); *B01J 13/206* (2013.01);

*C11D 3/001* (2013.01); *C11D 3/3726* (2013.01); *C11D 3/505* (2013.01); *C11D 17/0039* (2013.01)

(58) Field of Classification Search
CPC ......... A61K 9/5031; B01J 13/14; B01J 13/16; B01J 13/206
USPC ......... 264/4.1, 4.3, 4.33; 424/451, 452, 455, 424/490; 428/402.2
See application file for complete search history.

(56) References Cited

U.S. PATENT DOCUMENTS

| | | | |
|---|---|---|---|
| 2,800,457 | A | 7/1957 | Green et al. |
| 4,144,268 | A | 3/1979 | Guise |
| 4,855,490 | A | 8/1989 | Markusch et al. |
| | | (Continued) | |

FOREIGN PATENT DOCUMENTS

| | | |
|---|---|---|
| EP | 0537467 B1 | 10/1996 |
| EP | 1958627 A1 | 8/2008 |
| | (Continued) | |

OTHER PUBLICATIONS

M.F. Sonnenschein, 2015 "Introduction to Polyurethane Chemistry", Polyurethanes: Science, Technology, Markets, and Trends, First Edition. pp. 105-126.

(Continued)

*Primary Examiner* — Leo B Tentoni
(74) *Attorney, Agent, or Firm* — McDonnell Boehnen Hulbert & Berghoff LLP

(57) ABSTRACT

The present invention relates to a process for the preparation of biodegradable polyurea/polyurethane microcapsules, preferably perfume-containing polyurea/polyurethane microcapsules, which have a balance of biodegradability, stability and performance compared to prior art microcapsules. In addition, the present invention relates to biodegradable polyurea/polyurethane microcapsules comprising at least one lipophilic active ingredient obtainable by the process of the invention. In another aspect, the invention described herein relates to the use of such microcapsules or microcapsule dispersions comprising the microcapsules according to the invention for the manufacture of household products, textile care products, detergents, fabric softeners, cleaning agents, scent boosters, scent lotion or scent enhancers, cosmetics, personal care products, agricultural products or pharmaceutical products. Ultimately, the present invention relates to consumer products comprising such microcapsules or microcapsule dispersions.

20 Claims, 6 Drawing Sheets

(56) References Cited

U.S. PATENT DOCUMENTS

| | | | |
|---|---|---|---|
| 2009/0256107 A1* | 10/2009 | Hentze | B01J 13/14 |
| | | | 252/73 |
| 2010/0273887 A1 | 10/2010 | Machinek et al. | |
| 2017/0216802 A1 | 8/2017 | Siewert et al. | |
| 2017/0252274 A1 | 9/2017 | Lei et al. | |

FOREIGN PATENT DOCUMENTS

| | | | |
|---|---|---|---|
| EP | 2033688 | A2 | 3/2009 |
| JP | H09263624 | A | 10/1997 |
| JP | 2003326850 | A | 11/2003 |
| JP | 2014507433 | A | 3/2014 |
| JP | 2018518479 | A | 7/2018 |
| NZ | 286779 | A | 2/1997 |
| WO | 03015910 | A1 | 2/2003 |
| WO | 03099005 | A1 | 12/2003 |
| WO | 2004026840 | A1 | 4/2004 |
| WO | 2004098767 | A1 | 11/2004 |
| WO | 2007096592 | A1 | 8/2007 |
| WO | 2011160733 | A1 | 12/2011 |
| WO | 2011161229 | A1 | 12/2011 |
| WO | 2012107323 | A1 | 8/2012 |
| WO | 2018006089 | A1 | 1/2018 |
| WO | 2019243426 | A1 | 12/2019 |
| WO | 2020131879 | A2 | 6/2020 |

OTHER PUBLICATIONS

K.C. Frisch, et al., 1970, "Catalysis in Isocyanate Reactions", Journal of Macromolecular Science, Part C5(1) Polymer Reviews, pp. 103-149.

* cited by examiner degree of cross-linking

- - - Capsule stability

—— Sensoric performance

·········· Biodegradability

BIODEGRADABLE POLYUREA/POLYURETHANE MICROCAPSULES

CROSS-REFERENCE TO RELATED APPLICATIONS

This application is the US national phase under 35 U.S.C. § 371 of International Application No. PCT/EP2020/072206, filed Aug. 6, 2020, the contents of which are hereby incorporated by reference in their entirety.

The present invention relates to a process for preparing biodegradable polyurea/polyurethane microcapsules enclosing at least one lipophilic active ingredient, preferably perfume- or aroma-containing polyurea/polyurethane microcapsules, which have a balance of biodegradability, stability and performance compared to prior art microcapsules. In addition, the present invention relates to biodegradable polyurea/polyurethane microcapsules comprising at least one lipophilic active agent obtainable by the process of the invention. In another aspect, the invention described herein relates to the use of such microcapsules or microcapsule dispersions comprising the microcapsules according to the invention for the manufacture of household products, textile care products, detergents, fabric softeners, cleaning products, scent boosters, scent lotions or fragrance enhancers, cosmetics, personal care products, agricultural products, pharmaceutical products or printing coatings for paper. Ultimately, the present invention relates to consumer products comprising such microcapsules or microcapsule dispersions.

Microcapsules are particles consisting of a core and a wall material surrounding the core, where the core can be a solid, liquid or gaseous substance surrounded by a polymeric dense, permeable or semi-permeable wall material. During manufacture, after emulsification and coacervation or interfacial polymerisation, the polymers from the starting ingredients precipitate onto the substances to be encapsulated, which are thereby immobilised. The core is also called the inner phase. Names such as outer phase, shell or coating are also used for the wall. The diameter of the microcapsules typically varies in the range of 1 to 1000 µm. The wall thickness is typically 0.5 to 150 µm. Loadings of 25 to 95 wt % are typically possible, but also those of 1 to 99 wt %.

The aim of encapsulation is, among other things, to protect the encapsulated active substances or active ingredients, to release them at a specific time, to convert liquids into a manageable powder form, to delay the loss of volatile components (e.g. in the case of fragrances or flavourings), to prevent premature chemical reactions with other mixture components or to ensure better handling before or during processing. Hydrophobic active ingredients, such as fragrances or flavourings, can be easily incorporated into numerous and different application formulations through encapsulation.

The contents of microcapsules can be released in various ways and are based in particular on one of the mechanisms described below: mechanical destruction of the capsule by crushing or shearing; destruction of the capsule by melting of the wall material, destruction of the capsules by dissolution of the wall material or diffusion of the active substances through the capsule wall.

A variety of shell materials are known for the production of microcapsules. The shell can consist of either natural, semi-synthetic or synthetic materials. Natural shell materials are, for example, gum arabic, agar-agar, agarose, maltodextrins, alginic acid or its salts, e.g. sodium alginate or calcium alginate, fats and fatty acids, cetyl alcohol, collagen, chitosan, lecithins, gelatine, albumin, shellac, polysaccharides such as starch or dextran, polypeptides, protein hydrolysates, sucrose and waxes. Semisynthetic shell materials include, but are not limited to, chemically modified celluloses, in particular cellulose esters and cellulose ethers, e.g. cellulose acetate, ethyl cellulose, hydroxypropyl cellulose, hydroxypropyl methyl cellulose and carboxymethyl cellulose, and starch derivatives, in particular starch ethers and starch esters. Synthetic shell materials are, for example, polymers such as polyacrylates, polyamides, polyvinyl alcohol or polyvinylpyrrolidone.

Depending on the type of shell material and manufacturing process, microcapsules are produced with different properties in terms of diameter, size distribution and physical and/or chemical properties.

Polyurea microcapsules or polyurea/polyurethane microcapsules formed by polymerisation between a polyisocyanate and a polyamine and/or a diol or polyol are known capsules used in a variety of technical fields, including perfumery.

Polyurea microcapsules obtained by reacting two polyisocyanates and a polyamine are described, for example, in WO 2011/161229 or WO 2011/160733. According to WO 2011/161229 or WO 2011/160733, the polyurea microcapsules are prepared in the presence of polyvinylpyrrolidone (PVP) as a protective colloid. WO 2012/107323 discloses polyurea microcapsules having a polyurea shell comprising the reaction product of a polyisocyanate with guanazole (3,5-diamino)-1,2,4-triazole) and an amino acid in the presence of anionic stabilisers or surfactants such as anionic polyvinyl alcohol. EP 0 537 467 B describes microcapsules prepared from polyisocyanates containing polyethylene oxide groups in the presence of stabilisers such as polyvinyl alcohol. According to WO 2007/096592, microencapsulation may take place in an oil phase emulsified in a continuous aqueous phase generally stabilised by a surfactant system such as polyvinyl alcohols or carboxylated and sulphonated derivatives thereof.

The exemplary prior art delivery systems described above exhibit both good stability, namely the ability to retain the active ingredient and thus the ability of the capsules to avoid loss of the volatile components, and good performance, for example fragrance release in the case of fragrance capsules.

However, the microcapsules of the prior art described above have the disadvantage that the polymeric capsule wall or capsule shell material requires a large polymer content in order to ensure sufficient stability and not to suffer too great a loss of active ingredient. In addition, microencapsulation introduces plastic into the environment, where it can cause problems as "microplastic".

Because plastic particles are increasingly the subject of public criticism with regard to their environmental impact, and the demand for bio-based and biodegradable solutions is growing due to the steadily increasing social pressure with regard to environmental aspects, there is a need for microencapsulation to develop new materials in order to achieve a reduction of microplastics in the environment. Biobased and biodegradable materials are the focus here.

Against this background, there is therefore a need for the provision of polyurea/polyurethane microcapsules with outstanding stability and release properties for the respective applications on the one hand, and polyurea/polyurethane microcapsules that are predominantly or almost completely biodegradable on the other.

However, this task of using biodegradable materials to reduce the amount of microplastics in the environment is not trivial in the case of microencapsulations, as the desired functionality of the microcapsule, such as olfactory properties and positive secondary properties such as high stability, toxicological stability, conflicts with the requirements for rapid biodegradability in many applications.

It is particularly difficult to produce microcapsules that have both good stability and good active ingredient release. The ability to retain the active ingredient and thus the ability of the capsules to avoid the loss of the volatile components depends in particular on the stability of the capsules in the product base. However, capsules with good stability in particular do not automatically exhibit good biodegradability.

As the degree of cross-linking increases, the stability of the microcapsules increases, but at the same time the ability to biodegrade the capsule shell decreases. With very stable microcapsules, the performance, for example sensory performance, is lower, as the number of microcapsules that break open due to pressure, friction, etc. and release active ingredients decreases. If they are too unstable, they are already destroyed during storage and also do not perform well.

Against this background, the present invention was based on the complex task of providing a process for the production of microcapsules which, on the one hand, makes it possible to provide microcapsules with a lower polymer content which, at the same time, have a balanced ratio of high stability and excellent release behaviour of the encapsulated active substances and good biodegradable properties.

Surprisingly, it was found that this task can be solved by producing the polyurea/polyurethane microcapsules using amino acids and a release agent, which is incorporated into the microcapsule shell. The stability and sensory performance of the microcapsules can be further improved or optimised with a specific pH value adjustment during emulsification and cross-linking. Through the optional use of a further, i.e. second, catalyst, even microcapsules with an even better stability and performance can be achieved.

SUMMARY OF THE INVENTION

The present problem is solved by the objects of the independent patent claims. Preferred embodiments result from the wording of the dependent patent claims and the following description.

A first object of the present invention therefore relates to a process for preparing a biodegradable polyurea/polyurethane microcapsule comprising the following steps in this order:

(a) carrying out a first polymerisation and/or cross-linking step comprising:

(a1) providing an internal non-aqueous phase comprising at least one polyisocyanate having two or more isocyanate groups and at least one lipophilic active substance to be encapsulated;

(a2) providing an external aqueous phase comprising at least one protective colloid and optionally an emulsifier, and adjusting the pH of the aqueous phase to a pH of from 1 to 5;

(a3) mixing the internal non-aqueous phase and the external aqueous phase to obtain an oil-in-water emulsion or dispersion;

(a4) adding at least one first amino acid or amino acid hydrochloride and a first catalyst and adjusting the pH of the emulsion or dispersion to a pH of 4 to 8;

(b) carrying out a second polymerisation and/or cross-linking step by adding at least one hydroxyl group donor;

(c) carrying out a third polymerisation and/or crosslinking step by adding at least one second amino acid and adjusting the pH of the emulsion or dispersion to a pH of 4 to 8, in particular at a temperature of at least 60° C., to obtain a microcapsule dispersion;

(d) optionally adding another catalyst and adjusting the pH of the microcapsule dispersion to a pH of 4 to 7;

(e) curing the microcapsule dispersion obtained from step (c) or (d) at a temperature of at least 60° C. for a period of at least 60 minutes;

(f) addition of at least one release agent and incorporation of the release agent into the microcapsule shell;

(g) post-curing of the microcapsule obtained in step (f); and optional:

(h) separating the microcapsule from the microcapsule dispersion and, if necessary, drying the microcapsule or adjusting the viscosity of the microcapsule slurry by adding a thickening agent.

It is also an object of the invention described herein to provide a biodegradable polyurea/polyurethane microcapsule comprising at least one lipophilic active ingredient, prepared according to the process of the invention.

Another aspect of the present invention is a biodegradable polyurea/polyurethane microcapsule comprising (i) a core comprising at least one hydrophobic agent; and (ii) a capsule shell comprising:

a reaction product of a polymerisation and/or cross-linking of at least one polyisocyanate having two or more isocyanate groups, in the presence of at least one protective colloid with at least one first amino acid or an amino acid hydrochloride, a further polymerisation and/or cross-linking with at least one hydroxyl group donor, and a still further polymerisation and/or cross-linking with at least one second amino acid; and at least one release agent.

Finally, in another aspect, the present invention relates to the use of the biodegradable polyurea/polyurethane microcapsule or a dispersion of the polyurea/polyurethane microcapsules according to the invention for the manufacture of household products, textile care products, detergents, fabric softeners, cleaning agents, scent boosters, scent lotions or scent enhancers, cosmetics, personal care products, perfume compositions, agricultural products, pharmaceutical products or print coatings for paper, and the consumer products made therefrom.

Surprisingly, it was found within the scope of the present invention that, in the production of microcapsules, the combination of targeted polymerisation and/or crosslinking of polyisocyanates having at least two or more isocyanate groups with a first amino acid or an amino acid hydrochloride, subsequent polymerisation and/or crosslinking with a hydroxyl group donor and still further polymerisation and/or crosslinking with a second amino acid and the addition of a release agent and incorporation of the release agent into the microcapsule shell and targeted pH adjustment of the emulsion or dispersion at the beginning of emulsification and at the beginning of the respective crosslinking reactions leads to stable microcapsules and thus an efficient encapsulation of lipophilic active substances with subsequent targeted release of these active substances. Dispersion at the beginning of the emulsification and at the beginning of the respective cross-linking reactions leads to stable microcapsules and thus an efficient encapsulation of lipophilic active substances with subsequent targeted release of these active substances can be ensured, while at the same time the microcapsules exhibit good biodegradability due to their biobased and biodegradable building blocks, such as amino acids and release agents.

By using amino acids and a release agent, the polyiso-cyanate-polymer content of the capsule wall or capsule shell material can also be reduced, i.e. replaced by bio-based capsule wall components, without compromising the stabil-ity of the microcapsule wall. The incorporation of the release agent into the microcapsule shell also facilitates the biode-gradability of the capsule wall or capsule shell material.

These and other aspects, features and advantages of the present invention will be apparent to those skilled in the art from a study of the following detailed description and claims. In this regard, any feature from one aspect of the invention may be used or substituted in another aspect of the invention. The examples herein illustrate the invention with-out limiting it.

The terms "at least one" or "not less than one" or "one or more" as used herein refers to 1 or more, for example 2, 3, 4, 5, 6, 7, 8, 9 or more.

The term "and/or" expresses that a linkage exists, or an alternative is offered.

Numeric examples given in the form "x to y" include the values given. If multiple preferred numeric ranges are given in this format, all ranges created by combining the different endpoints are also included.

FIGURES

FIG. 1 is a light microscope image of the microcapsules according to the invention. The microcapsules were pre-pared from hexamethylene diisocyanate and 4,4'-methyldi-phenylene diisocyanate in a ratio of 75:25. Furthermore, lysine*HCl was used as the first amino acid, glycerol as the hydroxyl group donor and histidine as the second amino acid. DABCO was used as catalyst and a modified starch as protective colloid; beeswax was added as separating agent. An Olympus BX51 was used for the light microscopic image. The bar shown corresponds to 50 μm.

FIG. 2 shows a diagram of the particle size distribution (d(0.5)-value) of microcapsules according to the invention and microcapsules of the prior art based on polyurea/polyurethane structures without release agent. A MALVERN Mastersizer 3000 was used to determine the particle size distribution. The corresponding calculation is based on the Mie theory.

Figure 1:
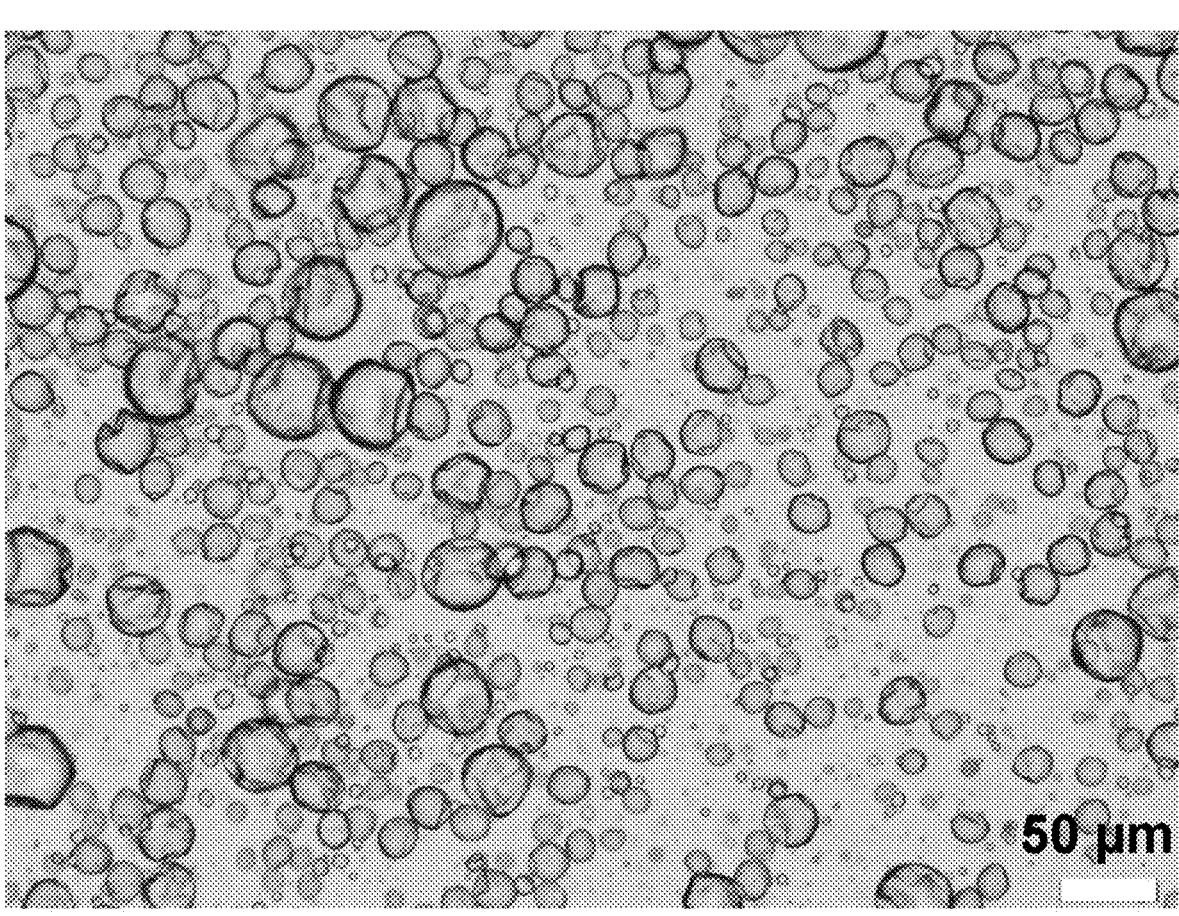

A dot is used as a decimal separator in each of the figures.

DETAILED DESCRIPTION OF THE INVENTION

In a first aspect, the present invention relates to a process for preparing a biodegradable polyurea/polyurethane micro-capsule, preferably a process for preparing a fragrance or flavour capsule, comprising the following steps in this order:

(a) carrying out a first polymerisation and/or cross-linking step comprising:

(a1) providing an internal non-aqueous phase comprising at least one polyisocyanate having two or more isocya-nate groups and at least one lipophilic active substance to be encapsulated;

(a2) providing an external aqueous phase comprising at least one protective colloid and optionally an emulsi-fier, and adjusting the pH of the aqueous phase to a pH of from 1 to (a3) mixing the internal non-aqueous phase and the exter-nal aqueous phase to obtain an oil-in-water emulsion or dispersion;

(a4) adding at least one first amino acid or amino acid hydrochloride and a first catalyst and adjusting the pH of the emulsion or dispersion to a pH of 4 to 8;

(b) carrying out a second polymerisation and/or cross-linking step by adding at least one hydroxyl group donor;

(c) carrying out a third polymerisation and/or crosslinking step by adding at least one second amino acid and adjusting the pH of the emulsion or dispersion to a pH of 4 to 8, in particular at a temperature of at least 60° C., to obtain a microcapsule dispersion;

(d) optionally adding another catalyst and adjusting the pH of the microcapsule dispersion to a pH of 4 to 7;

(e) curing the microcapsule dispersion obtained from step (c) or (d) at a temperature of at least 60° C. for a period of at least 60 minutes;

(f) addition of at least one release agent and incorporation of the release agent into the microcapsule shell;

(g) post-curing of the microcapsule obtained in step (f); and optional:

(h) separating the microcapsule from the microcapsule dispersion and, if necessary, drying the microcapsule or adjusting the viscosity of the microcapsule slurry by adding a thickening agent.

In the context of the present invention, microcapsules are understood to be microparticles which have a capsule shell or capsule wall and at least one or more active ingredients as core material inside the capsule. The active ingredients are preferably lipophilic or hydrophobic active ingredients. Such active ingredients are not or only poorly soluble in water but are readily soluble in fats and oils. The terms "microcapsule" or "capsule" and "lipophilic" or "hydropho-bic" are used synonymously in the present invention.

In the context of the present invention, the capsule shell or capsule wall is preferably composed of several crosslink-ing matrices or crosslinking units, which preferably have different compositions and are generated by several process steps or process sequences, in particular crosslinking steps, during the production of the microcapsule according to the invention, so that a three-dimensional network is formed.

A cross-linking matrix or cross-linking unit in the context of the present invention is a composite or network of starting components for building the microcapsule shell, which is built up by linear or three-dimensional polymerisation and/or cross-linking between functional groups of the starting components and/or with other components of the microcapsule shell and/or in which other components of the microcapsule shell are embedded. Several cross-linking matrices can in turn be cross-linked with each other by further cross-linking in the course of the process according to the invention and form a three-dimensional structure for building the microcapsule shell or microcapsule wall. The cross-linking units or cross-linking matrices form the capsule shell or capsule wall in their entirety.

In an even more preferred embodiment of the present invention, the capsule shell or capsule wall comprises at least polyurea and polyurethane crosslinking matrices or crosslinking units and a release agent incorporated into the capsule shell or capsule wall.

In a first step (a) of the process according to the invention, a first polymerisation and/or crosslinking (a) is carried out. For this purpose, an internal non-aqueous phase is provided (a1), which comprises at least one isocyanate or a polyisocyanate with two or more isocyanate groups and at least one lipophilic active substance to be encapsulated.

The polyurea/polyurethane microcapsules according to the present invention are prepared using at least one or more polyisocyanates.

The at least one isocyanate or polyisocyanate having two or more isocyanate groups, which is used in the method of the invention for the preparation of a biodegradable polyurea/polyurethane microcapsule, has at least two isocyanate groups for forming polymeric networks by polymerisation, which form a capsule shell or capsule wall.

Polyisocyanates are R-substituted organic derivatives (R—N═C═O) of isocyanic acid (HN═C═O). Organic isocyanates are compounds in which the isocyanate group (—N═C═O) is bonded to an organic radical. Polyfunctional isocyanates or polyisocyanates are those compounds which contain at least two or more, i.e. 3, 4, 5, 6, 7, 8, 9, 10, 11, 12, 13, 14, 15, 20, 50, 100, 200 or even more, isocyanate groups (—N═C═O) in the molecule. Polyisocyanates with two isocyanate groups are also called diisocyanates.

Polyisocyanates can be classified as aliphatic, cycloaliphatic, hydroaromatic, aromatic or heterocyclic isocyanates or polyisocyanates. In addition, the polyisocyanates according to the invention can be linear or branched.

Polyisocyanates, especially aromatic polyisocyanates, are highly reactive compounds. The polyaddition reactions of polyisocyanates with diols or polyols are the basis of polyurethane chemistry and the polyaddition reactions of polyisocyanates with amines are the basis of polyurea chemistry.

According to the invention, at least difunctional, preferably polyfunctional polyisocyanates are used, i.e. all aliphatic, alicyclic and aromatic isocyanates are suitable, provided they have at least two reactive isocyanate groups.

Aliphatic, cycloaliphatic, hydroaromatic, aromatic or heterocyclic polyisocyanates, their substitution products and mixtures of the aforementioned monomeric or oligomeric compounds are particularly preferred. Of the polyisocyanates specified above, aliphatic and/or aromatic compounds are preferably used.

In preferred embodiments of the process according to the invention, the polyisocyanate contains on average 2 to 5 functional —N═C═O groups. These include, for example, aliphatic, cycloaliphatic and aromatic di-, tri- and higher polyisocyanates.

Among the above-mentioned polyisocyanates, diisocyanates and polyisocyanates with three functional —N—C═O groups are particularly preferred and therefore find priority application in the implementation of the present invention. Preferably, diisocyanates with the general structure O═C═N—R—N═C═O, where R stands for aliphatic, alicyclic or aromatic radicals, are used. Preferably, the radicals have five or more carbon atoms.

In a preferred embodiment of the process according to the invention, the at least one polyisocyanate having two or more isocyanate groups is selected from the group consisting of aliphatic polyisocyanates and/or aromatic polyisocyanates. In an even more preferred variant of the process according to the invention, the at least one polyisocyanate is a combination of two different aliphatic polyisocyanates or a combination of an aliphatic and aromatic polyisocyanate.

Due to the number of functional groups, optimal crosslinking or networking of the capsule wall is achieved, providing microcapsules that exhibit prolonged slow release of active ingredients as well as good stability in the consumer product.

In a preferred variant of the process according to the invention, the polyisocyanate is an aliphatic polyisocyanate.

The term "aliphatic polyisocyanate" refers to any polyisocyanate molecule that is not aromatic. In addition, the molecule comprises at least two isocyanate groups, i.e. at least 2, 3, 4, 5, 6, 7, 8, 9, 10, 11, 12, 13, 14, 15, 20, 50, 100, 200 or more isocyanate groups directly attached to a corresponding number of different C atoms of the same aliphatic molecule, and derivatives of such compounds.

The aliphatic polyisocyanate molecule having at least two isocyanate groups, i.e. at least 2, 3, 4, 5, 6, 7, 8, 9, 10, 11, 12, 13, 14, 15, 20, 50, 100, 200 or more isocyanate groups, may further be linear, branched or cyclic and may have any substitutions including, for example, aliphatic substituents, aromatic substituents, one or more heteroatoms such as nitrogen, oxygen, phosphorus and/or sulphur, halogens such as fluorine, chlorine, bromine and/or iodine and/or other functional groups such as alkoxy groups.

The linear aliphatic polyisocyanate molecule is preferably selected from C2 to C20 linear alkyl, preferably C3 to C15 linear alkyl, C4 to C12 linear alkyl, C5 to C10 linear alkyl, C6 to C9 linear alkyl or C7 to C8 linear alkyl. Preferably, the linear aliphatic molecule does not comprise an aromatic structure.

The branched aliphatic polyisocyanate molecule is preferably selected from C2 to C20 branched alkyl, preferably C3 to C15 branched alkyl, C4 to C12 branched alkyl, C5 to C10 branched alkyl, C6 to C9 branched alkyl, C7 to C8 branched alkyl.

The shorter the carbon chain of the polyisocyanate molecule, the higher the reaction rate compared to longer-chain analogues.

The cyclic aliphatic polyisocyanate molecule comprises at least 1, i.e. 1, 2, 3, 4 or more non-aromatic ring structures, the ring structure itself preferably consisting only of C atoms. Of course, the C atoms of the ring structure may carry suitable substituents. The at least 1 ring structures preferably consist independently of 3, 4, 5, 6, 7 or 8-membered rings. Preferably, the cyclic aliphatic molecule comprises 2 to 20 C atoms, such as 3 to 15 C atoms, 4 to 12 C atoms, 5 to 10 C atoms, 6 to 9 C atoms or 7 to 8 C atoms.

In a further variant of the process according to the invention, the polyisocyanate is an aromatic polyisocyanate. The term "aromatic polyisocyanate" refers to any polyisocyanate compound in which two or more isocyanate groups are directly attached to aromatic C atoms and comprise, for example, a phenyl, tolyl, xylyl, naphthyl or diphenyl moiety as the aromatic component, and derivatives of such polyisocyanate compounds.

Aromatic polyisocyanates react significantly faster than aliphatic polyisocyanates and are therefore preferably used in the process according to the invention.

The linear, branched or cyclic aliphatic or aromatic polyisocyanate may be present as a monomer or polymer. A monomeric polyisocyanate is a molecule that is not linked to another molecule, in particular not by one or more cross-linking agents. A polymeric polyisocyanate comprises at least two monomers linked by one or more cross-linking agents. The at least two monomers need not necessarily be the same monomers, but may be different. A polymeric polyisocyanate preferably comprises at least 2 or more monomers, i.e. at least 2, 3, 4, 5, 10, 20, 30, 40, 50, 100 or more monomers linked together by at least one cross-linking agent.

The linear, branched or cyclic aliphatic or aromatic polyisocyanate preferably has a limited size/molecular weight, which allows reactivity with the one or more crosslinking agents. Examples of suitable molecular weights preferably comprise ca. 100 g/mol to $5\cdot10^4$ g/mol, preferably 120 g/mol to $2\cdot10^4$ g/mol, 140 g/mol to $10^4$ g/mol, 160 g/mol to $5\cdot10^3$ g/mol, 180 g/mol to $2\cdot10^3$ g/mol, 200 g/mol to $10^3$ g/mol, 220 g/mol to 900 g/mol, 240 g/mol to 800 g/mol, 260 g/mol to 700 g/mol, 280 g/mol to 600 g/mol, 300 g/mol to 500 g/mol, 320 g/mol to 450 g/mol or 340 g/mol to 400 g/mol.

Any number of different linear, branched and/or cyclic aliphatic and/or aromatic polyisocyanates may be used. For example, at least one, i.e. at least 1, 2, 3, 4, 5, 6, 7, 8, 9 or 10 different linear aliphatic polyisocyanates is used. For example, at least one, i.e. at least 1, 2, 3, 4, 5, 6, 7, 8, 9 or 10 different branched aliphatic polyisocyanates is used. For example, at least one, i.e. at least 1, 2, 3, 4, 5, 6, 7, 8, 9 or 10 different branched cyclic polyisocyanates is used.

Preferably, derivatives of linear, branched and/or cyclic aliphatic polyisocyanates are used. A derivative, as used herein, is understood in its broadest sense as a compound derived from a compound by a chemical reaction. Examples of derivatives include oligomers and/or adducts of the linear or branched aliphatic polyisocyanates mentioned above. Preferred oligomers are biurets, isocyanurates, uretdiones, iminooxadiazinediones and preferred adducts are trimethylolpropane adducts. These oligomers/adducts are well known in the prior art and disclosed for example in U.S. Pat. No. 4,855,490 A or U.S. Pat. No. 4,144,268 A.

Preferably, the aliphatic polyisocyanate is present only in monomeric form and/or dimerised form (as isocyanate) or in oligomeric form.

The derivatives of linear, branched or cyclic polyisocyanates and/or mixtures thereof can also be obtained by reacting the polyisocyanates with polyalcohols (e.g. glycerol), polyamines, polythiols (e.g. dimercaprol).

The isocyanate compounds as defined above specifically include the various isomers, if present, alone or in combination. For example, methylenebis(cyclohexylisocyanate) (H12MDI) comprises 4,4'-methylenebis(cyclohexylisocyanate), 2,4'-methylenebis(cyclohexylisocyanate) and/or 2,2'-methylenebis(cyclohexylisocyanate).

Exemplary aliphatic polyisocyanates include those commercially available such as. BAYHYDUR N304 and BAYHYDUR N3Q5 which are aliphatic water dispersible polyisocyanates based on hexamethylene diisocyanate, DESMODUR N3400, DESMODUR N3600, DESMODUR N3700 and DESMODUR N3900 which are low viscosity, polyfunctional aliphatic polyisocyanates based on hexamethylene diisocyanate, and DESMODUR 3600 and DESMODUR N100 which are aliphatic polyisocyanates based on hexamethylene diisocyanate, each of which is available from Bayer Corporation, Pittsburgh, PA.

According to another preferred variant of the present invention, the linear or branched aliphatic polyisocyanates is or are selected from the group consisting of pentamethylene diisocyanate (PDI, such as Stabio D-370N or D-376N from Mitsui Chemicals Inc., Japan), hexamethylene diisocyanate (HDI), ethyl ester lysine triisocyanate, lysine diisocyanate ethyl ester and derivatives thereof, preferably wherein each of said derivatives comprises more than one isocyanate group and optionally further comprises one or more groups selected from the group consisting of biuret, t, isocyanurate, uretdione, iminooxadiazinedione and trimethylolpropane adduct and/or wherein said cyclic aliphatic polyisocyanate or cyclic aliphatic polyisocyanates are selected from the group consisting of isophorone diisocyanate (IPDI), 1,3-bis (isocyanatomethyl) cyclohexane (H6XDI, such as Takenate) or is selected from 600 Mitsui Chemicals Inc., Japan), 1,2-bis (isocyanatomethyl) cyclohexane, 1,4-bis (isocyanato-methyl) cyclohexane, methylenebis (cyclohexyl isocyanate)) (H12MDI) and derivatives thereof, preferably wherein each of said derivatives comprises more than one isocyanate group and optionally further comprises one or more groups selected from the group consisting of biuret, isocyanurate, uretdione, iminooxadiazinione and trimethylolpropane adduct (such as TMP adduct) of H6XDI, in particular Takenate D-120N of Mitsui Chemicals Inc, Japan).

Aliphatic polyisocyanates obtained from renewable raw materials such as PDI (Stabio D-370N or D-376N from Mitsui Chemicals Inc., Japan) are particularly preferred. It was found that such aliphatic polyisocyanates obtained from renewable raw materials do not affect the quality/properties of the core-shell capsules.

Other suitable commercially available polyisocyanates include LUPRANAT M20 (BASF) where the average n is 0.7; PA PI 27 (Dow Chemical) where the average n is 0.7; MONDUR MR (Bayer) where the average n is 0.8; MONDUR MR Light (Bayer) with an average n of 0.8; MONDUR 489 (Bayer) where the average n is 1.0; poly-[(phenyl isocyanate)-co-formaldehyde (Aldrich Chemical, Milwaukee, WI), other isocyanate monomers such as DESMODUR N3200 (Bayer) and TAKENATE D1 10-N(Mitsui Chemicals Corporation, Rye Brook, NY). Other representative polyisocyanates include polyisocyanates named TAKENATE D-1 10N (Mitsui), DESMODUR L75 (Bayer) and DESMODUR IL (Bayer).

In a preferred embodiment, the polyisocyanate used in the preparation of the polyurea/polyurethane microcapsules according to the present invention is used as the sole polyisocyanate component, i.e. without the admixture of any other polyisocyanate component different therefrom.

Examples of the monomeric polyisocyanates which can be used according to the invention, and which contain at least two polyisocyanate groups are:

Ethylene diisocyanate, trimethylene diisocyanate, 1,4-tetramethylene diisocyanate, 1,6-hexamethyldiisocyanate, ethylene diisothiocyanate, tetramethylene diisothiocyanate, hexamethylene diisothiocyanate, cyclobutane-1,3-diisocyanate, cyclohexane-1,3-diisocyanate, cyclohexane-1,4-diisocyanate, 1,3-phenylene diisocyanate, 1,4-phenylene diisocyanate, mixtures of 1,3-phenylene diisocyanate and 1,4-phenylene diisocyanate, p-phenylene diisothiocyanate, xylylene-1,4-diisothiocyanate, 2,4-toluylene diisocyanate, 2,6-toluylene diisocyanate, mixtures of 2,4-toluylene diisocyanate and 2,6-toluylene diisocyanate, xylylene-1,4-diiso-cyanate, xylylene-1,3-diisocyanate and mixtures of xylylene-1,4-diisocyanate and xylylene-1,3-diisocyanate, 2,4-hexahydrotoluylene diisocyanate, 2,6-hexahydro-toluylene diisocyanate, mixtures of 2,4-hexahydrotoluylene diisocyanate and 2,6-hexahydrotoluylene diisocyanate, hexahydro-1,3-phenylene diisocyanate, hexahydro-1,4-phe-nylene diisocyanate, mixtures of hexahydro-1,4-phenylene diisocyanate and hexahydro-1,4-phenylene diisocyanate, 1,3-diisocyanatobenzene, 1,3,5-trimethylbenzene-2,4-diiso-cyanate, 1,3,5-triisopropylbenzene-2,4-diisocyanate, diphe-nylmethane-4,4'-diisocyanate, 3,3'-dimethyldiphenylmeth-ane-4,4'-diisocyanate, 4,4'-diphenylpropane diisocyanate, naphthylene-1,4-diisocyanate, naphthylene-1,5-diisocya-nate, triphenylmethane-4,4',4"-triisocyanate, toluene-2,4,6-triisocyanate, dimethyldiphenylmethane-2,2',5,5'-tetraiso-cyanate or mixtures of the aforementioned compounds.

As polymerisable compounds containing at least two polyisocyanate groups, preference is given to di- and polyi-socyanates produced on a large scale, for example TDI: Toluylene diisocyanate (isomer mixture of 2,4- and 2,6-toluylene diisocyanate in a ratio of 80:20), HDI: Hexam-ethylene diisocyanate-(1,6), IPDI: Isophorone diisocyanate or DMDI: Diphenylmethane-4,4'-diisocyanate.

Other preferred monomeric polyisocyanate compounds are: Diisocyanates such as 1,4-diisocyanatobutane, 1,6-dii-socyanatohexane, 1,5-diisocyanato-2,2-dimethylpentane, 2,2,4- and 2,4,4-trimethyl-1,6-diisocyanatohexane, 1,10-dii-socyanatodecane, 1,3- and 1,4-diisocyanatocyclohexane, 1-polyisocyanato-3,3,5-trimethyl-5-polyisocyanatomethyl-cyclohexane (isophorone diisocyanate), 4,4'-diisocyanatodi-cyclohexylmethane, 2,4- and 2,6-diisocyanatomethylcyclo-hexane and mixtures thereof. In principle, aromatic polyisocyanates, e.g. toluylene diisocyanates or 4,4'-diiso-cyanatodiphenylmetha can also be used.

Other specific examples of diisocyanates comprise, for example, 1,5-naphthylene diisocyanate, 4,4'-diphenylmeth-ane diisocyanate (MDI), hydrogenated MDI (H12MDI), xylylene diisocyanate tetramethylxylene (TMXD1) (XDI), diisocyanate 4,4'-diphenyldimethylmethane diisocyanate, di- and tetraalkyldiphenylmethane diisocyanate, 4,4'-diben-zyldiisocyanate, 1,3-phenylene diisocyanate, 1,4-phenylene diisocyanate, the isomers of toluylene diisocyanate (TDI), optionally in a mixture, 1-methyl-2,4-diisocyanatocyclo-hexane, 1,6-diisocyanato-2,2,4-trimethylhexane, 1,6-diiso-cyanato-2,4,4-trimethylhexane, 1-isocyanatomethyl-3-iso-cyanato-1,5,5-trimethylcyclohexane, chlorinated and brominated diisocyanates, phosphorus-containing diisocya-nates, 4,4'-diisocyanatophenylperfluoroethane, tetram-ethoxybutane-1,4-diisocyanate, butane-1,4-diisocyanate, (HDI), dicyclohexylmethane diisocyanate, cyclohexane-1,4-diisocyanate, ethylene diisocyanate, phthalic acid bisiso-cyanatoethyl ester, also polyisocyanates with reactive halo-gen atoms such as 1-chloromethylphenyl-2,4-diisocyanate-1,2-br 3,3-bischloromethyl ether-4,4'-diphenyl diisocyanate.

It has been surprisingly shown that in particular the use of longer-chain aliphatic diisocyanates with six, seven, eight, nine, ten or even more carbon atoms leads to the formation of more stable capsule shells or capsule walls.

In a particularly preferred embodiment, the internal non-aqueous phase comprises a mixture of two or more different polymerisable polyisocyanates, for example polyisocya-nates with different chain lengths, which can form copoly-mers.

Proportionally, derivatives of polyisocyanates which can be prepared by modification of the above-mentioned diiso-cyanates or mixtures thereof by known methods and which contain, for example, uretdione, urethane, isocyanurate, biuret and/or allophanate groups can also be used in the process according to the invention.

A combination of at least two different, preferably ali-phatic, polyisocyanates or a combination of at least one aliphatic and at least one aromatic polyisocyanate is par-ticularly preferred.

In such a combination, the different reaction rates of the polyisocyanates are exploited: Aromatic polyisocyanates react significantly faster than aliphatic polyisocyanates and for the short-chain aliphatic polyisocyanates, i.e. aliphatic polyisocyanates with one to five carbon atoms, preferably three to five carbon atoms, the reaction rate is higher compared to longer-chain analogues.

In another preferred embodiment of the invention, the different aliphatic and/or aromatic polyisocyanates therefore also have different chain lengths. Longer chain polyisocya-nates in this context preferably have six, seven, eight, nine, ten, eleven, twelve, thirteen, fourteen, twenty, twenty-five or more carbon atoms, but more preferably they have six to twelve carbon atoms and particularly preferably six to eight carbon atoms. By shorter chain polyisocyanates is meant polyisocyanates having one to five carbon atoms and pref-erably polyisocyanates having three to five carbon atoms.

Preferred according to the invention is a combination of a short-chain aliphatic polyisocyanate (C1, C2, C3, C4, C5) and a long-chain aliphatic polyisocyanate (C6, C7, C8, C9, C10, C11, C12, C13, C14, C15, C20, C25 or more) or a combination of a short-chain aliphatic polyisocyanate (C1, C2, C3, C4, C5) (C1, C2, C3, C4, C5) with a long-chain aromatic polyisocyanate (C6, C7, C8, C9, C10, C11, C12, C13, C14, C15, C20, C25 or more) or a combination of a long-chain aliphatic polyisocyanate (C6, C7, C8, C9, C10, C11, C12, C13, C14, C15, C20, C25 or more) with a short chain aromatic polyisocyanate.

Particularly preferred in this context is the use of a mixture of different aliphatic polyisocyanates having two or more isocyanate groups with chain lengths of one to twelve carbon atoms in the chain, preferably three to eight carbon atoms and particularly preferably four to seven carbon atoms, for the production of the biodegradable microcap-sules according to the invention.

Aliphatic polyisocyanates are particularly preferable in this context due to their chemical relationship to biobased systems. For example, both lysine and 1,5-diisocyanatopen-tane show the same degradation product, 1,5-diaminopen-tane, and are therefore particularly suitable for use in the production of biobased and biodegradable microcapsules, taking environmental considerations into account.

Primary embodiments comprise mixtures of longer-chain and shorter-chain diisocyanates in any mixing ratio. Prefer-ably, the mixing ratio of longer-chain diisocyanates to shorter-chain diisocyanates is in a range from 4:1 to 1:4 and particularly preferably from 2:1 to 1:2.

Examples of preferred specific mixtures of at least one aliphatic polyisocyanate and of at least one aromatic polyi-socyanate are a mixture of a biuret of hexamethylene diisocyanate with a trimethylol adduct of xylylene diisocya-nate, a mixture of a biuret of hexamethylene diisocyanate with a polyisocyanurate of diisocyanate or a mixture of a biuret of hexamethylene diisocyanate with a trimethylolpro-pane adduct of toluene diisocyanate.

According to the invention, it is even more preferred if, in the combination of a short-chain aliphatic polyisocyanate and a long-chain aliphatic polyisocyanate described above or in the combination of a short-chain aliphatic polyisocya-nate and a long-chain aromatic polyisocyanate or in the combination of a long-chain aliphatic polyisocyanate with a short-chain aromatic polyisocyanate, the polyisocyanates are in a mixture of monomeric or oligomeric or polymeric form.

Preferably, this results in the following combinations for use in the process according to the invention:

short-chain aliphatic polyisocyanate (monomer or oligomer or polymer) and short-chain aliphatic polyisocyanate (monomer or oligomer or polymer);

short-chain aliphatic polyisocyanate (monomer or oligomer or polymer) and long-chain aliphatic polyisocyanate (monomer or oligomer or polymer);

short-chain aliphatic polyisocyanate (monomer or oligomer or polymer) and short-chain aromatic polyisocyanate (monomer or oligomer or polymer);

short-chain aliphatic polyisocyanate (monomer or oligomer or polymer) and long-chain aromatic polyisocyanate (monomer or oligomer or polymer);

long-chain aliphatic polyisocyanate (monomer or oligomer or polymer) and short-chain aliphatic polyisocyanate (monomer or oligomer or polymer);

long-chain aliphatic polyisocyanate (monomer or oligomer or polymer) and long-chain aliphatic polyisocyanate (monomer or oligomer or polymer);

long-chain aliphatic polyisocyanate (monomer or oligomer or polymer) and short-chain aromatic polyisocyanate (monomer or oligomer or polymer);

long-chain aliphatic polyisocyanate (monomer) and long-chain aromatic polyisocyanate (oligomer or polymer);

with the previously described definitions for short-chain and long-chain.

It could be observed that the choice of at least two aliphatic polyisocyanates of different chain length and degree of polymerisation or the choice of mixtures of aliphatic and aromatic polyisocyanates lead to a significant gain in stability and performance (fragrance release in the case of fragrance capsules) due to the different reaction rates of the polyisocyanate components, dissociations and cross-linking structures.

With the above-mentioned polyisocyanate combinations or polyisocyanate mixtures of two different aliphatic or one aliphatic and one aromatic polyisocyanate, particularly stable and better, i.e. more densely branched cross-links can be produced within the capsule shell.

Thus, with the method described herein, performant (fragrance release) microcapsules can be produced, which are either made from a mixture of an aliphatic and aromatic polyisocyanate or from a mixture of two different aliphatic polyisocyanates. Such microcapsules are very stable and are characterised by outstanding fragrance storage properties, which in turn is reflected in a better performance (fragrance release) of the capsules, for example in the field of fragrance or fragrance encapsulation.

The use of two different polyisocyanates results in microcapsules that again exceed the stability of microcapsules made from single polyisocyanate systems, as illustrated in the following embodiments.

The microcapsule made of an aliphatic-aliphatic polyisocyanate mixture is just as good as a microcapsule made of an aliphatic-aromatic polyisocyanate mixture, as illustrated in the following embodiment examples. Accordingly, in principle, the combination of at least two different polymerisable (preferably aliphatic and/or aromatic) polyisocyanates is preferred in the present invention.

The content of polyisocyanate for the preparation of the microcapsule according to the invention is 0.1 to 10.0 wt.-%, preferably 0.5 to 3.0 wt.-%, based on the total weight of the internal non-aqueous phase.

The proportion of the polyisocyanate component to the internal non-aqueous phase is preferably between 1:50 and 1:20, even more preferably between 1:40 and 1:30.

Due to the low proportion of the polyisocyanate component, it is possible according to the present invention to produce polyurea/polyurethane microcapsules in which the absolute polyisocyanate proportion is only $\frac{1}{50}$th—of the total capsule comprising at least one lipophilic active substance to be encapsulated. Thus, polyurea/polyurethane microcapsules having a polyisocyanate content of only 0.6 wt.-%, based on the total weight of the capsule wall, can be produced by the process according to the invention. Preferably, the polyisocyanate content is about 1.8 wt.-% of the capsule wall. Despite the low polyisocyanate content, the microcapsules according to the invention are nevertheless characterised by a high stability.

In step (a1) of the process for producing the microcapsules according to the invention, the at least one polymerisable polyisocyanate comprising at least two or more functional isocyanate groups is first substantially dissolved together with at least one or more active ingredient(s) to be encapsulated, optionally in an inert, non-aqueous solvent or a solvent mixture of inert, non-aqueous solvents. By "substantially dissolved" it is understood that at least 90 wt.-%, preferably at least 98 wt.-%, more preferably 99.9 wt.-%, of the aforementioned ingredients are dissolved in the solvent or in the solvent mixture to be able to use them in the present process. Preferably, the at least one polyisocyanate and the at least one active ingredient to be encapsulated are completely dissolved in the solvent or in the solvent mixture. If a solvent does not ensure sufficient solubility of the isocyanates, it is possible to overcome this disadvantage by using suitable solubility promoters.

Preferred solvents for the internal non-aqueous phase are immiscible with water and do not react with the isocyanate component(s) or the active ingredient component(s) and have little or no odour in the amounts used.

The term "solvent" in the context of the present invention comprises all types of oil bodies or oil components, in particular vegetable oils such as e.g. rapeseed oil, sunflower oil, soybean oil, olive oil and the like, modified vegetable oils, e.g. alkoxylated sunflower or soybean oil, synthetic (tri) glycerides such as e.g. technical mixtures of mono-, di- and triglycerides of C6 to C22 fatty acids, fatty acid alkyl esters, e.g. methyl or ethyl esters of vegetable oils. e.g. technical mixtures of mono-, di- and triglycerides of C6 to C22 fatty acids, fatty acid alkyl esters, e.g. methyl or ethyl esters of vegetable oils (Agnique® ME 18 RD-F, Agnique® ME 18 SD-F, Agnique® ME 12C-F, Agnique® ME1270), fatty acid alkyl esters based on these C6 to C22 fatty acids, mineral oils and mixtures thereof. Examples of suitable and preferred lipophilic solvents are: Guerbet alcohols based on fatty alcohols with 6 to 18, preferably 8 to 10, carbon atoms, esters of linear C6 to C22 fatty acids with linear or branched C6 to C22 fatty alcohols or esters of branched C6 to C13 carboxylic acids with linear or branched C6 to C22 fatty alcohols, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl stearate, stearyl erucate, isostearyl myristate, isostearyl palmitate, isostearyl stearate, isostearyl isostearate, isostearyl oleate, isostearyl behenate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

Also suitable are esters of linear C6 to C22 fatty acids with branched alcohols, in particular 2-ethylhexanol, esters of C18 to C38 alkyl hydroxycarboxylic acids with linear or branched C6 to C22 fatty acids, in particular dioctylalate, esters of linear or branched fatty acids with polyhydric alcohols (such as propylene glycol, dimer diol or trimer triol) and/or Guerbet alcohols, triglycerides based on C6 to C10 fatty acids, liquid mono-/di-/triglyceride mixtures of C6 to C18 fatty acids, esters of C6 to C22 fatty alcohols and/or Guerbet alcohols with aromatic carboxylic acids, in particular benzoic acid, esters of C2 to C12 dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear or branched C6 to C22 fatty alcohol carbonates, such as dicaprylyl carbonate (Cetiol® CC); Guerbet carbonates based on fatty alcohols with 6 to 18, preferably 8 to 10 carbon atoms, benzoic acid esters with linear or branched C6 to C22 alcohols, linear or branched, symmetrical or asymmetrical dialkyl ethers with 6 to 22 carbon atoms per alkyl group, such as dicaprylyl ethers, ring-opening products of epoxidised fatty acid esters with polyols, silicone oils (cyclomethicones, silicone methicone grades etc.), aliphatic or naphthenic hydrocarbons, such as squalane, squalene or dialkylcyclohexanes and/or mineral oils.

Preferred solvents are in particular also esters of linear C6 to C22 fatty acids with branched alcohols, esters of C18 to C38 alkyl hydroxycarboxylic acids with linear or branched C6 to C22 fatty alcohols, linear or branched C6 to C22 fatty alcohols, in particular dioctyl malates, esters of linear or branched fatty acids with polyhydric alcohols, such as e. g. propylene glycol, dimer diol or trimer triol, and/or Guerbet alcohols, triglycerides based on C6- to C10-fatty acids, liquid mono-/di-/triglyceride mixtures based on C6- to C18-fatty acids, esters of C6- to C22-fatty alcohols and/or Guerbet alcohols with aromatic carboxylic acids, in particular benzoic acid, esters of C2- to C12-dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched C6- to C22-fatty alcohol carbonates, such as e.g. dicaprylyl carbonate (Cetiol™ CC), Guerbet carbonates based on fatty alcohols with 6 to 18, preferably 8 to 10, carbon atoms, esters of benzoic acid with linear or branched C6 to C22 alcohols, linear or branched, symmetrical or asymmetrical dialkyl ethers with 6 to 22 carbon atoms per alkyl group, such as e.g. dicaprylyl ether (Cetiol™ OE), ring opening products of epoxidised fatty acid esters with polyols, silicone oils (cyclomethicones, silicon methicone types, etc.) and/or aliphatic or naphthenic hydrocarbons, such as squalane, squalene or dialkylcyclohexanes.

Furthermore, liquid linear and/or branched and/or saturated or unsaturated hydrocarbons or any desired mixtures thereof may be used as solvents within the scope of the present invention. These may be, for example, alkanes having 4 to 22, preferably 6 to 18 carbon atoms, or any mixtures thereof.

Particularly advantageous inert solvents for the internal non-aqueous phase are alkyl aromatic hydrocarbons such as diisopropyl naphthalene or substituted biphenyls, chlorinated diphenyl, paraffins, chlorinated paraffin, natural vegetable oils such as cottonseed oil, peanut oil, palm oil, tricresyl phosphate, silicone oil, dialkyl phthalates, dialkyl adipates, partially hydrogenated terphenyl, alkylated biphenyl, alkylated naphthalene, diaryl ether, aryl alkyl ether and higher alkylated benzene, benzyl benzoate, isopropyl myristate as well as any mixtures of these hydrophobic solvents and mixtures of single or several of these hydrophobic solvents with kerosene, paraffins and/or isoparaffins. Preferably, vegetable oils such as sunflower oil, triglycerides, benzyl benzoate or isopropyl myristate are used as solvents for providing the internal non-aqueous phase.

The solvents mentioned above are used in the process according to the invention either individually or as a mixture of two or more solvents.

In an alternative and preferred variant of the process according to the invention, the at least one polyisocyanate is dissolved directly in a solution of the at least one active ingredient, preferably one or more fragrances or flavours or a perfume oil, so that essentially no solvent, as described above, is present in the core of the microcapsule according to the invention. The avoidance of a solvent in the microcapsule core is advantageous in that it reduces manufacturing costs and addresses environmental concerns.

The fragrance compounds or flavourings are dissolved in particular in solvents that are commonly used in the perfume or flavouring industry. The solvent is preferably not an alcohol since alcohols react with the isocyanates. Examples of suitable solvents are diethyl phthalate, isopropyl myristate, Abalyn® (rosin resins, available from Eastman), benzyl benzoate, ethyl citrate, limonene or other terpenes or isoparaffins. Preferably, the solvent is highly hydrophobic. Preferably, the fragrance or flavouring solution comprises less than 30% solvent. More preferably, the fragrance or flavouring solution comprises less than 20% and even more preferably less than 10% solvent, all such percentages being defined by weight relative to the total weight of the fragrance or flavouring solution. Most preferably, the fragrance or flavouring is substantially free of solvent.

The active substance to be encapsulated or the core material for the production of the microcapsules according to the invention can basically be any material suitable for inclusion in microcapsules in the process according to the invention. The active ingredients to be encapsulated are lipophilic, water-insoluble or water-immiscible liquids or solids as well as suspensions. This ensures that the active ingredient to be encapsulated is in the internal non-aqueous phase during production of the microcapsule according to the invention and does not mix with the external aqueous phase, as otherwise no emulsion can form and no deposition of the capsule wall material can take place on the droplet surface. This results in the lipophilic active ingredient being completely enclosed inside the microcapsule as core material during the subsequent emulsification and cross-linking of the capsule wall components. The internal non-aqueous phase thus formed is characterised by its organically hydrophobic, oily character.

In a particularly preferred variant of the present invention, the at least one lipophilic or hydrophobic active substance is in particular a lipophilic or hydrophobic fragrance or aroma substance or a lipophilic or hydrophobic perfume oil or aroma (fragrance or aroma mixture), a cooling agent, a TRPV1 or a TRPV3 modulator, a substance which causes a pungent taste or a warmth or heat sensation on the skin or mucous membranes or a tingling or prickling sensation in the mouth or throat, or an active substance with a pungent or acrid or astringent effect, a pesticide, a biocide, an insecticide, a substance from the group of repellents, a food additive, a cosmetic active ingredient, a pharmaceutical active ingredient, a dye, a dye precursor, a luminous paint, an agrochemical, an optical brightener, a solvent, a wax, a silicone oil, a lubricant, a substance for printing coatings for paper, or a mixture of two or more of the abovementioned active substances.

In a preferred variant of the present invention, lipophilic active ingredients are in particular lipophilic fragrance compounds or fragrance mixtures of two or more fragrances (perfume oils) or flavourings or flavouring mixtures of two or more flavourings (aromas) or also biogenic principles.

It is particularly preferred that the core comprises one or more fragrance(s) or aroma(s) selected from the group consisting of: Extracts of natural raw materials and also fractions thereof or constituents isolated therefrom; individual fragrances from a group of hydrocarbons; aliphatic alcohols; aliphatic aldehydes and acetals; aliphatic ketones and oximes; aliphatic sulphur-containing compounds; aliphatic nitriles; esters of aliphatic carboxylic acids; formates, acetates, propionates, isobutyrates, butyrates, isovalerates, pentanoates, hexanoates, crotonates, tiglinates and 3-methyl-2-butenoates of acyclic terpene alcohols; acyclic terpene aldehydes and ketones and their dimethyl and diethyl acetals; formates, acetates, propionates, isobutyrates, butyrates, isovalerates, pentanoates, hexanoates, crotonates, tiglinates and 3-methyl-2-butenoates of cyclic terpene alcohols; cyclic terpene aldehydes and ketones; cyclic alcohols; cyclic and cycloaliphatic ethers; cyclic and macrocyclic ketones; cycloaliphatic aldehydes; cycloaliphatic ketones; esters of cyclic alcohols; esters of cycloaliphatic carboxylic acids; aromatic hydrocarbons; araliphatic alcohols; esters of araliphatic alcohols and aliphatic carboxylic acids; araliphatic ethers; aromatic and araliphatic aldehydes; aromatic and araliphatic ketones; aromatic and araliphatic carboxylic acids and esters thereof; nitrogen-containing aromatic compounds; phenyl ethers and phenyl esters; heterocyclic compounds; lactones; and mixtures of the foregoing.

Suitable fragrance compounds and flavourings for the production of the capsules according to the invention are preferably described, for example, in "Fragrances", in Steffen Arctander, in "Perfume and Flavor Chemicals", self-published, Montclair, N.J. 1969; H. Surburg, J. Panten, in "Common Fragrance and Flavor Materials", 5th edition, Wiley-VCH, Weinheim 2006.

Preferably, the microcapsules according to the invention comprise a core material in the form of a hydrophobic single fragrance or single aroma, wherein the core material comprises at least one single fragrance or single aroma selected from one or more of the following groups:

Hydrocarbons, such as 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

Aliphatic alcohols, such as hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3,4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

Aliphatic aldehydes and their acetals, such as hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanaldiethylacetal; 1,1-dimethoxy-2,2,5-trimethyl-4-hexene; citronellyloxyacetaldehyde; 1-(1-methoxypropoxy)-(E/Z)-3-hexene;

Aliphatic ketones and their oximes, such as 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

Aliphatic sulphur-containing compounds, such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

Aliphatic nitriles, such as 2-nonenoic acid nitrile; 2-tridecenoic acid nitrile; 2,12-tridecenoic acid nitrile; 3,7-dimethyl-2,6-octadienoic acid nitrile; 3,7-dimethyl-6-octenoic acid nitrile;

Aliphatic carboxylic acids and their esters, such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; ethyl octanoate; ethyl (E,Z)-2,4-decadienoate; in particular ethyl 2-trans-4-cis-decadienoate; methyl 2-octinate; methyl 2-noninate; allyl 2-isoamyloxyacetate; methyl 3,7-dimethyl-2,6-octadienoate; 4-methyl-2-pentyl crotonate;

Acyclic terpene alcohols, such as citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-Dimethyl-3,5-octadien-2-ol; 3,7-Dimethyl-4,6-octadien-3-ol; 3,7-Dimethyl-1,5,7-octatrien-3-ol; 2,6-Dimethyl-2,5,7-octatrien-I-ol; and their formates, acetates, propionates, isobutyrates, butyrates, isovalerates, pentanoates, hexanoates, crotonates, tiglinates or 3-methyl-2-butenoates;

Acyclic terpene aldehydes and ketones, such as geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl and diethylacetals of geranial, neral, 7-hydroxy-3,7-dimethyloctanal; in particular the dimethyl and diethylacetals of geranial, neral and 7-hydroxy-3,7-diemthylactanal;

Cyclic terpene alcohols, such as menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiaol; and their formates, acetates, propionates, isobutyrates, butyrates, isovalerates, pentanoates, hexanoates, crotonates, tiglinates or 3-methyl-2-butenoates;

Cyclic terpene aldehydes and ketones, such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; beta-irone; alpha-damascenone; beta-damascenone;

gamma-damascenone; delta-damascenone; gamma-Damascenon; 1-(2,4,4-Trimethyl-2-cyclohexen-1-yl)-2-buten-1-one; 1,3,4,6,7,8a-Hexahydro-1,1,5,5-tetramethyl-2H-2,4a-methanonaphthalen-8(5H)-one; 2-methyl-4-(2,6,6-trimethyl-1-cyclohexen-1-yol)-2-butenal; nootkatone; dihydronootkatone; 4,6,8-metgastigmatrien-3-one; alpha-sinensal; beta-sinensal; acetylated cedarwood oil (methylcedryl ketone);

Cyclic alcohols, such as 4-tert-butylcyclohexanol; 3,3,5-trimethylcyclohexanol; 3-isocamphylcyclohexanol; 2,6,9-trimethyl-(Z2,Z5,E9)cyclododecatrien-1-ol; 2-isobutyl-4-methyltetrahydro-2H-pyran-4-ol; from the group of cycloaliphatic alcohols such as. 3,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-Ethyl-4-(2,2,3-trimethyl-3-cyclopent-1-yl)-2-buten-1-ol; 3-Methyl-5-(2,2,3-trimethyl-3-cyclopent-1-yl)-pentan-2-ol; 3-Methyl-5-(2,2,3-trimethyl-3-cyclopent-1-yl)-4-penten-2-ol; 3,3-Dimethyl-5-(2,2,3-trimethyl-3-cyclopent-1-yl)-4-penten-2-ol; 1-(2,2,6-Trimethylcyclohexyl)pentan-3-ol; 1-(2,2,6-Trimethylcyclohexyl)hexan-3-ol;

Cyclic and cycloaliphatic ethers, such as cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

Cyclic and macrocyclic ketones, such as 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

Cycloaliphatic aldehydes, such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones, such as 1-(3,3-dimethylcyclohexyl)-4-penten-1-one; 2,2-dimethyl-1-(2,4-dimethyl-3-cyclohexen-1-yl)-1-1propanone; 1-(5,5-dimethyl-2-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl)ketone;

Esters of cyclic alcohols, such as 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5-resp.-6-indenyl acetate; 4,7- methano-3a,4,5,6,7,7a-hexahydro-5-resp.-6-indenyl propionate; 4,7-methano-3a,4,5,6,7,7a-hexahydro-5-resp.-6-indenyl isobutyrate; 4,7-methanooctahydro-5-resp.-6-indenyl acetate;

esters of cycloaliphatic alcohols, such as 1-cyclohexyl-ethyl crotonate;

Esters of cycloaliphatic carboxylic acids, such as allyl 3-cyclohexyl propionate; allyl cyclohexyloxy acetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic hydrocarbons, such as styrene and diphenylmethane;

Araliphatic alcohols, such as benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenyl-ethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids, such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; α-trichloromethyl benzyl acetate; a,a-dimethylphenylethyl acetate; a,a-dimethylphenylethyl butyrate; cinnamyl acetate; 2-phenoxyethyl isobutyrate; 4-methoxybenzyl acetate;

Araliphatic ethers, such as, for example, 2-phenylethyl methyl ether; 2-phenylethyl isoamyl ether; 2-phenylethyl 1-ethoxyethyl ether; phenylacetaldehyde dimethylacetal; phenylacetaldehyde diethylacetal; hydratropaaldehyde dimethylacetal; phenylacetaldehyde glycerolacetal; 2,4,6-trimethyl-4-phenyl-1,3-dioxanes; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes, such as benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)-propanal; 2-methyl-3-(4-tert-butylphenyl)propanal; 3-(4-tert-butylphenyl)propanal; Cinnamaldehyde; a-butylcinnamaldehyde; a-amylcinnamaldehyde; a-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

Aromatic and araliphatic ketones, such as acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthon;

Aromatic and araliphatic carboxylic acids and esters thereof, such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenyl glycidate; ethyl 3-methyl-3-phenyl glycidate;

Nitrogen-containing aromatic compounds, such as 2,4,6-trinitro-1,3-dimethyl-5-tert-butylbenzene; 3,5-dinitro-2,6-dimethyl-4-tert-butyl acetophenone; cinnamic acid nitrile; 5-phenyl-3-methyl-2-pentenoic acid nitrile; 5-phenyl-3-methylpentanoic acid nitrile; methyl anthranilate; methyl N-methyl anthranilate; Schiff bases of methylanthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; scatole; 2-methoxy-3-isopropylpyrazine; 2-isobutyl-3-methoxypyrazine; 4-(4,8-dimethyl-3,7-nonadienyl)-pyridine;

Phenols, phenyl ethers and phenyl esters, e.g. tarragol; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate; from the group of heterocyclic compounds such as e.g. 2,5-Dimethyl-4-hydroxy-2H-furan-3-one; 2-Ethyl-4-hydroxy-5-methyl-2H-furan-3-one; 3-Hydroxy-2-methyl-4H-pyran-4-one; 2-Ethyl-3-hydroxy-4H-pyran-4-one;

Lactones, such as e.g. 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 1,15-pentadecanolide; cis- and trans-11-pentadecene-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin;

as well as the stereoisomers, enantiomers, positional isomers, diastereomers, cis/trans isomers or epimers of the aforementioned substances; and mixtures of the aforementioned substances.

In a further variant of the process according to the invention, flavouring substances can also be encapsulated as a core material in the form of a single flavouring, wherein the core material comprises at least one single flavouring substance or mixtures thereof as active substance.

Typical examples of flavouring substances or flavourings which can be encapsulated in the sense of the invention are selected from the group consisting of: acetophenone; allyl capronate; alpha ionone; beta ionone; anisaldehyde; anisyl acetate; anisyl formate; benzaldehyde; benzothiazole; benzyl acetate; benzyl alcohol; benzyl benzoate; beta ionone; butyl butyrate; butyl capronate; butylidene phthalide; carvone; camphene; caryophyllene; cineol; cinnamyl acetate; citral; citronellol; citronellal; citronellyl acetate; cyclohexyl acetate; cymene; damascone; decalactone; dihydrocoumarin; dimethyl anthranilate; dimethyl anthranilate; dodecalactone; ethoxyethyl acetate; ethyl butyric acid; ethyl butyrate; ethyl caprinate; ethyl capronate; ethyl crotonate; ethyl furaneol; ethyl guaiacol; ethyl isobutyrate; ethyl isovalerate; ethyl lactate; ethyl methyl butyrate; ethyl propionate; eucalyptol; eugenol; ethyl heptylate; 4-(p-hydroxyphenyl)-2-butanone; gamma-decalactone; geraniol; geranyl acetate; geranyl acetate; grapefruit aldehyde; methyl dihydrojasmonate (e.g. Hedion®); heliotropin; 2-heptanone; 3-heptanone; 4-heptanone; trans-2-heptenal; cis-4-heptenal; trans-2-hexenal; cis-3-hexenol; trans-2-hexenoic acid; trans-3-hexenoic acid; cis-2-hexenyl acetate; cis-3-hexenyl acetate; cis-3-hexenyl capronate; trans-2-hexenyl capronate; cis-3-hexenyl formate; cis-2-hexyl acetate; cis-3-hexyl acetate; trans-2-hexyl acetate; cis-3-hexyl formate; para-hydroxybenzylacetone; isoamyl alcohol; isoamyl isovalerate; isobutyl butyrate; isobutyraldehyde; isoeugenol methyl ether; isopropyl methyl thiazole; lauric acid; leavulinic acid; linalool; linalool oxide; linalyl acetate; menthol; menthofuran; methyl anthranilate; methyl butanol; methyl butyric acid; 2-methyl butyl acetate; methyl capronate; methyl cinnamate; 5-methyl furfural; 3,2,2-methylcyclopentenolone; 6,5,2-methylheptenone; methyl dihydrojasmonate; methyl jasmonate; 2-methyl methyl butyrate; 2-methyl-2-pentenoic acid; methyl thiobutyrate; 3,1-methylthiohexanol; 3-methylthiohexyl acetate; nerol; nerylacetate; trans, trans-2,4-nonadienal; 2,4-nonadienol; 2,6-nonadienol; 2,4-nonadienol; nootkatone; delta-octalactone; gamma-octalactone; 2-octanol; 3-octanol; 1,3-octenol; 1-octyl acetate; 3-octyl acetate; palmitic acid; paraldehyde; phellandrene; pentanedione; phenylethyl acetate; phenylethyl alcohol; phenylethyl alcohol; phenylethyl isovalerate; piperonal; propionaldehyde; propyl butyrate; pulegone; pulegol; sinensal; sulfurol; terpinene; terpineol; terpinolene; 8,3-thiomenthanone; 4,4,2-thiomethylpentanone; thymol; delta-undecalactone; gamma-undecalactone; valencene; valeric acid; vanillin; acetoin; ethylvanillin; ethylvanillin isobutyrate (3-ethoxy-4-isobutyryloxybenzaldehyde); 2,5-dimethyl-4-hydroxy-3(2H)-furanone and its derivatives (preferably homofuraneol (2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone); maltol and maltol derivatives (preferably ethyl maltol); coumarin and coumarin derivatives; gamma-lactones (preferably gamma-undecalactone, gamma-nonalactone, gamma-decalactone); delta-lactones (preferably 4-methyldeltadecalactone, massoilactone, deltadecalactone, tuberolactone); methyl sorbate; divanillin; 4-hydroxy-2(or 5)-ethyl-5(or 2)-methyl-3(2H)furanone; 2-hydroxy-3-methyl-2-cyclopentenone; 3-hydroxy-4,5-dimethyl-2(5H)-furanone; acetic acid isoamyl ester; butyric acid ethyl ester; butyric acid n-butyl ester; butyric acid isoamyl ester; 3-methyl butyric acid ethyl ester; n-hexanoic acid ethyl ester; n-hexanoic acid allyl ester; n-hexanoic acid n-butyl ester; n-octanoic acid ethyl ester; ethyl 3-methyl-3-phenyl glycidate; ethyl 2-trans-4-cis-decadienoate; 4-(p-hydroxyphenyl)-2-butanone; 1,1-dimethoxy-2,2,5-trimethyl-4-hexane; 2,6-dimethyl-5-hepten-1-al; phenylacetaldehyde; 2-methyl-3-(methylthio)furan; 2-methyl-3-furanthiol; bis(2-methyl-3-furyl) disulfide; furfuryl mercaptan; methional; 2-acetyl-2-thiazoline; 3-mercapto-2-pentanone; 2,5-dimethyl-3-furanthiol; 2,4,5-trimethylthiazole; 2-acetylthiazole; 2,4-dimethyl-5-ethylthiazole; 2-acetyl-1-pyrroline; 2-methyl-3-ethylpyrazine; 2-ethyl-3,5-dimethylpyrazine; 2-ethyl-3,6-dimethylpyrazine; 2,3-diethyl-5-methylpyrazine; 3-isopropyl-2-methoxypyrazine; 3-isobutyl-2-methoxypyrazine; 2-acetylpyrazine; 2-pentylpyridine; (E,E)-2,4- decadienal; (E,E)-2,4-nonadienal; (E)-2-octenal; (E)-2-non-enal; 2-undecenal; 12-methyltridecanal; 1-penten-3-one; 4-hydroxy-2,5-dimethyl-3(2H)-furanone; guaiacol; 3-hy-droxy-4,5-dimethyl-2(5H)-furanone; 3-hydroxy-4-methyl-5-ethyl-2(5H)-furanone; cinnamaldehyde; cinnamalcohol; methyl salicylate; isopulegol as well as the stereoisomers, enantiomers, positional isomers, diastereomers, cis/trans isomers or epimers of these substances not explicitly men-tioned herein; and mixtures of the aforementioned sub-stances.

Of the aforementioned individual fragrances which can be encapsulated in the sense of the present invention, prefer-ence is given to fragrance componds which have an alde-hyde, carboxylic acid or ester functionality.

Aldehydic fragrances, which also include the correspond-ing acetals as well as esters and lactones, can be divided into the following groups, namely (i) aliphatic aldehydes and their acetals;
    (ii) cycloaliphatic aldehydes;
    (iii) aromatic or araliphatic aldehydes;
    (iv) aliphatic, aromatic or araliphatic esters; and
    (v) Lactones;
and mixtures thereof.

The aforementioned fragrances with aldehyde, carboxylic acid or ester functionality, and mixtures thereof, are selected from one or more of the following groups:

Aliphatic aldehydes and their acetals, such as e.g. hexa-nal; heptanal; octanal; nonanal; decanal; undecanal; dodecanal; tridecanal; 2-methyloctanal; 2-methylnona-nal; (f)-2-hexenal; (Z)-4-heptenal; 2,6-dimethyl-5-hep-tenal; 10-undecenal; (f)-4-decenal; 2-dodecenal; 2,6, 10-trimethyl-5,9-undecadienal; heptanal diethylacetal; 1,1-dimethoxy-2,2,5-trimethyl-4-hexene; citronelly-loxyacetaldehyde;

Cycloaliphatic aldehydes, such as 2,4-dimethyl-3-cyclo-hexenecarbaldehyde; 2-methyl-4-(2,2,6-trimethyl-cy-clohexen-I-yl)-2-butenal; 4-(4-hydroxy-4-methylpen-tyl)-3-cyclohexenecarbaldehyde; 4-(4-methyl-3-penten-I-yl)-3-cyclohexenecarbaldehyde;

Aromatic and araliphatic aldehydes such as benzalde-hyde; phenylacetaldehyde; 3-phenylpropanal; hydra-tropaaldehyde; 4-methylbenzaldehyde; 4-methylphe-nylacetaldehyde; 3-(4-ethylphenyl)-2,2-dimethylpropanal; 2-methyl-3-(4-isopropylphenyl) propanal; 2-methyl-3-(4-te/t-butylphenyl)propanal; 3-(4-te/t-butylphenyl)propanal; cinnamaldehyde; α-butylcinnamaldehyde; α-amylcinnamaldehyde; α-hexylcinnamaldehyde; 3-methyl-5-phenylpentanal; 4-methoxybenzaldehyde; 4-hydroxy-3-methoxybenz-aldehyde; 4-hydroxy-3ethoxybenzaldehyde; 3,4-meth-ylenedioxybenzaldehyde; 3,4-dimethoxybenzalde-hyde; 2-methyl 3-(4-methoxyphenyl)propanal; 2-methyl 3-(4-methylenedioxyphenyl)propanal;

Aliphatic carboxylic acid esters, such as e. g. (E)- and (Z)-3-hexenyl formate; ethyl acetoacetate; isoamyl acetate; hexyl acetate; 3,5,5-trimethylhexyl acetate; 3-methyl-2-butenyl acetate; (f)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexano-ate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyac-etate; methyl 3,7-dimethyl 2,6-octadienoate;

Esters of cyclic alcohols, such as. 2-te/t-butyl cyclohexyl acetate; 4-te/t-butyl cyclohexyl acetate; 2-ieri-pentyl cyclohexyl acetate; 4-te/t-pentyl cyclohexyl acetate; decahydro-2-naphthyl acetate; 3-pentyl tetrahydro-2/-/-pyran-4-yl acetate; decahydro-2,5,5,8a-tetramethyl-2-naphthyl acetate; 4,7-methano-3a,4,5,6,7,7a-hexa-hydro-5-resp.-6-indenyl acetate; 4,7-methano-3a,4,5,6, 7,7a-hexahydro-5-resp.-6-indenyl propionate; 4,7-methano-3a,4,5,6,7,7a-hexahydro-5-resp.-6-indenyl isobutyrate; 4,7-methanooctahydro-5-resp.-6-indenyl acetate;

Esters of araliphatic alcohols and aliphatic carboxylic acids, such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; a-trichloromethyl benzyl acetate; α,α-dimethylpheny-lethyl acetate; α, α-dimethylphenylethyl butyrate; cin-namyl acetate; 2-phenoxyethyl isobutyrate; 4-methoxybenzyl acetate;

Esters of cycloaliphatic carboxylic acids, such as e.g. allyl 3-cyclohexyl propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic and araliphatic carboxylic acid esters, such as methyl benzoate; ethyl benzoate; hexyl benzoate; ben-zyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cin-namate; allyl phenoxy acetate; methyl salicylate; iso-amyl salicylate; hexyl salicylate; cyclohexyl salicylate; cis-3-hexenyl salicylate; benzyl salicylate; phe-nyl ethyl salicylate; methyl 2,4-dihydroxy-3,6-dimethyl benzoate; ethyl 3-phenyl glycidate; ethyl 3-methyl-3-phenyl glycidate.

Listed below are aldehydes, acetals, esters and lactones with their commercial designations which are particularly preferred as representatives of groups (i) to (v) for the purposes of the process according to the invention:

Aldehydes: 2-methylpentanal; Aldehyde C12 MNA HM; Aldehyde C 4; Aldehyde C 5; Aldehyde C 6; Aldehyde C 7; Aldehyde C 8; Aldehyde C 9; Aldehyde C 10; Aldehyde C 11 ISO; Aldehyde C 11 MOA PURE; Aldehyde C 11 UNDECANAL; Aldehyde C 11 UNDEYLENIC; Aldehyde C 12; Aldehyde C 12 MNA; Aldehyde C 13; ALDEHYDE MADARINE; AMYL CINNAMIC ALDEHYDE ALPHA; ANISALALDEHYDE-O; ANISYL ALDEHYDE; BENZ-ALDEHYDE NAT.; BERGAMAL; BORONAL; BOURGENOAL; CAMPHONELIC ALDEHYDE; CITRAL; CITRONELLAL HM; CITRONELLYL OXY-ACET ALDEHYDE; CITRYLAL; CITROYLAL E HM; CORTEX ALDEHYDE; CORTEX ALDEHYDE 50 PCT PEMOSA; CROTONIC ALDEHYDE; CUMINAL ALDE-HYDE; CYCLAMEN ALDEHYDE; DECADIENAL TRANS, TRANS-2,4, DECANAL CIS-4; DECANAL TRANS-2; DECANAL TRANS-2 NAT; DECANAL TRANS-4; DECANAL-9,1; DODECANIENAL 2,6; DODECANAL TRANS-2; DUPICAL; EPOXYDECE-NAL-4,5-2 10% TRI; ETHYL HEXANAL; FARENAL®; FLORHYDRAL; GERALDEHYDE; HELIONAL; HELIO-PAN; HELIOTROPIN; HEPTADIENAL TRANS, TRANS, 2-4; HEPTENAL CIS-4; HEPTENAL TRANS-2; HEX-ENAL TRANS-2; HEXYL CINNAMIC ALDEHYDE ALPHA; HYDRATROPIC ALDEHYDE; HYDROXY CIT-RONELLAL; INTRELEVEN ALDEHYDE SPEC.; ISONONYL ALDEHYDE; ISOVALERIC ALDEHYDE; LEMON ALDEHYDE H&R JS I; LILIAL; LINOLAL; LYRAL; MAJANTAL; MANDRINAL; MANDRAINE ALDEHYDE 10% IN TEC BHT; MEFRANAL; MEL-ONAL®; METHODY CITRONELLAL; METHYL BUTYRALDEHYDE; METHYL CINNAMIC ALDE-HYDE ALPHA; METHYL PHENYLPENTENAL-4,2,2; METHYL THIO PROPANAL-3; METHYL TRIDECA-NAL-12 10% VT; METHYL-3-BUTEN-2-AL; METHYL-5-PHENYL-2-HEXENE-2-AL; MUGENAL 50 DPG; NEOCYCLO CITRAL; NONADIENAL; TRANS,CIS-2,6; NONENAL CIS-6; NONENAL TRANS-2; ONCIDAL® 3/060251; PENTENAL TRANS-2; PERILLA ALDE-HYDE; PHENYLACET ALDEHYDE; PHENYLBUTE-NAL TRANS-2,2; PHENYLPROPYL ALDEHYDE; PINOACET ALDEHYDE; PROFRANESAL; PROPI-ONALALDEHYDE 2-(P-TOLYL); PROPIONIC ALDE-HYDE; PS-IRALDEIN X NEU; SAFRANAL; SALI-CYLIC ALDEHYDE FG; SILVIAL; TETRAHYDRO CITRAL; TIGLIC ALDEHYDE-2,2; TOLYL ALDEHYDE PARA FG; TRIDECENAL TRANS-2; TRIFERNAL; UNDECADIENAL-2,4; UNDECENAL TRANS-2; VER-NALALDEHYDE; VERTOCITRAL; VERTOMUGAL; VERTIPRENAL; VETRAL ROH; ZIMTALDEHYD NAT. HM; Acetals: FLOROPAL; HEPTANAL DIETHYL ACETAL; NONANDIENAL DIETHYL ACETAL; OKOU-MAL; PHENYLACET ALD. GLYCERIN ACETAL; PHE-NYLACETALDEYHDEDIMETHYLACETAL; Ester: JASMAL; JESSEMAL; KHARISMAL; TIRAMISONE®.

In an alternative embodiment, a fragrance mixture or a perfume oil or a flavouring mixture or a flavouring is used in the polyurea/polyurethane microcapsules according to the invention as the active substance to be encapsulated or as the core material. These are compositions which contain at least one fragrance or one aromatic substance. Such composi-tions, in particular perfume mixtures or perfume oils, pref-erably comprise two, three, four, five, six, seven, eight, nine, ten or even more perfumes. The fragrance mixtures or perfume oils Perfume oils are preferably selected from the group consisting of extracts of natural raw materials; essen-tial oils, concretes, absolutes, resins, resinoids, balsams, tinctures, such as ambergris tincture; amyris oil; angelica seed oil; angelica root oil; anise oil; armoise oil; valerian oil; basil oil; Tree moss absolute oil; Bay oil; Mugwort oil; Benzoin resin; Bergamot oil; Beeswax absolute oil; Birch tar oil; Bitter almond oil; Savory oil; Bucco leaf oil; Cabreuva oil; Cade oil; Calmus oil; Camphor oil; Cananga oil; Car-damom oil; Cascarilla oil; Cassia oil; Cassie absolute oil; Castoreum absolute oil; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolu; Oak moss absolu; Elemi oil; Tarragon oil; Eucalyptus citriodora oil; Eucalyptus oil; Fennel oil; Spruce needle oil; Fir needle oil; Galbanum oil; Galbanum resin; Geranium oil; Grapefruit oil; Guaiac wood oil; Gurjun balsam; Gurjun balsam oil, Helichrysum absolute; Helichrysum oil; Ginger oil; Iris root absolute; Iris root oil; Jasmine absolute; Calamus oil; Camomile oil blue; Camo-mile oil Roman; Carrot seed oil; Cascarilla oil; Pine needle oil; Curly mint oil; Caraway oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linal oil; Litsea cubeba oil; Laurel oil; Bay leaf oil; Macis oil; Marjoram oil;

Mandarin oil; Massoirinden oil; Mimosa absolute oil; Musk grain oil; Musk tincture; Muscat sage oil; Nutmeg oil; Myrrh absolute oil; Myrrh oil; Myrtle oil; Clove leaf oil; Clove blossom oil; Neroli oil; Olibanum absolute oil; Olibanum oil; Opopanax oil; Orange blossom absolute oil; Orange oil; Origanum oil; Palmarosa oil; Patchouli oil; Perilla oil; Perubalsam oil; Parsley leaf oil; Parsley seed oil; Petitgrain oil; Peppermint oil; Pepper oil; Allspice oil; Pine oil; Poley oil; Rose absolute oil; Rosewood oil; Rose oil; Rosemary oil; Sage oil Dalmatian; Sage oil Spanish; Sandalwood oil; Celery seed oil; Spicy lavender oil; Star anise oil; Styrax oil; Tagetes oil; Fir needle oil; tea tree oil; turpentine oil; thyme oil; tolu balsam; tonka oil; tuberose oil; vanilla extract; violet leaf oil; verbena oil; vetiver oil; juniper berry oil; wine yeast oil; wormwood oil; wintergreen oil; ylang ylang oil; hyssop oil; civet oil; cinnamon leaf oil; cinnamon bark oil; and fractions thereof or ingredients isolated therefrom. ingredients isolated therefrom.

Exemplary cooling agents used as lipophilic active ingre-dients in the manufacture of the microcapsules according to the invention comprise one or more of menthol and menthol derivatives (for example, L-menthol, D-menthol, racemic menthol, isomenthol, neoisomenthol, neomenthol), menthyl ether (for example (1-menthoxy)-2-propanediol, (1-men-thoxy)-2-methyl-1,2-propanediol, 1-menthyl methyl ether), menthyl ester (for example menthyl formate, menthyl acetate, menthyl isobutyrate, menthyl lactate, L-menthyl L-lactate, L-menthyl D-lactate, menthyl (2-methoxy) acetate, menthyl (2-methoxyethoxy) acetate, menthyl pyro-glutamate), menthyl carbonates (for example, menthyl pro-pylene glycol carbonate, menthyl ethylene glycol carbonate, menthyl glycerol carbonate or mixtures thereof), semiesters of menthol with a dicarboxylic acid or derivatives thereof (for example, monomenthyl succinate, monomenthyl glut-arate, monomenthyl malonate, O-menthyl succinate-N, N-(dimethyl) amide, O-menthyl succinamide), menthane carboxamides (for example, menthane carboxylic acid-N-ethylamide [WS3], N-alpha-(methane carbonyl) glycine ethyl ester [WS5], menthane carboxylic acid-N-(4-cyano-phenyl) amide, menthanecarboxylic acid-N-(alkoxyalkyl) amide), menthone and menthone derivatives (for example, L-menthone glycerol ketal), 2,3-dimethyl-2-(2-propyl)-bu-tanoic acid derivatives (for example, 2,3-dimethyl-2-(2-propyl)-butanoic acid-N-methylamide [WS23]), isopulegol or its esters (1-(–)-isopulegol, 1-(–)-isopulegol acetate), menthane derivatives (for example, p-menthane-3,8-diol), cubebol or synthetic or natural mixtures containing cubebol, pyrrolidone derivatives of cycloalkyldione derivatives (for example 3-methyl)-2-(1-pyrrolidinyl)-2-cyclopenten-1-one) or tetrahydropyrimidin-2-ones (for example icilin or related compounds as described in WO 2004/026840). Other cool-ing agents are menthol (L-menthol, D-menthol, racemic menthol, isomenthol, neoisomenthol, neomenthol), L-men-thyl methyl ether, menthyl formate, menthyl acetate), men-thone, isopulegol, L-(–)-isopulegol acetate) and cubebol, which have a cooling taste effect. Suitable cooling agents are well known in the art and are described for example in US 2017/216802 (A1), US 2010/273887 (A1), EP 2 033 688 (A2) and EP 1 958 627 (A2).

In an alternative variant, a TRPV1 or a TRPV3 modulator is used in the polyurea/polyurethane microcapsules accord-ing to the invention as the active substance to be encapsu-lated or as the core material. TRPV1 and TRPV3 modulators are known in the prior art and relate to TRP (Transient Receptor Potential) channels of the vanilloid (TRPV) sub-family. TRPV1 modulators impart a spicy taste and the hot sensation associated with capsaicin and piperine. The TRPV3 protein belongs to the family of non-selective cation channels that function in a variety of processes, including temperature sensation and vasoregulation. The TRPV3 channel is directly activated by several natural compounds such as carvacrol, thymol and eugenol. Some other monoterpenoids that either cause a sensation of warmth or are skin sensitizers can also open the channel. Monoterpenoids also induce agonist-specific desensitisation of TRPV3 channels in a calcium-independent manner.

In a further variant, the polyurea/polyurethane microcapsules according to the invention use, as active substance to be encapsulated or as core material, an active substance selected from the group consisting of substances which cause a pungent taste or a warmth or heat sensation on the skin or mucous membranes or a tingling or prickling sensation in the mouth or throat, or active substances with a pungent or acrid or astringent effect.

The heat-inducing or pungent active ingredients are preferably selected from the group consisting of: paprika powder, chilli pepper powder, extracts of paprika, extracts of pepper, extracts of chilli pepper, extracts of ginger roots, extracts of grains of paradise (Aframomum melegueta), extracts of para cress (Jambu oleoresin; Spilanthes acmella, resp. Spilanthes oleracea), extracts of Japanese pepper (Zanthoxylum piperitum), extracts of Kaempferia galanga, extracts of Alpinia galanga, extracts of water pepper (Polygonium hydropiper), capsaicinoids, especially capsaicin, dihydrocapsaicin or nonivamide; gingerols, in particular gingerol-[6], gingerol-[8], or gingerol-[10]; shogaols, in particular shogaol-[6], shogaol-[8], shogaol-[10]; gingerdiones, in particular gingerdione-[6], gingerdione-[8] or gingerdione-[10]; paradoles, in particular paradole-[6], paradole-[8] or paradole-[10]; dehydrogingerdiones, in particular dehydrogingerdione-[6], dehydrogingerdione-[8] or dehydrogingerdione-[10]; piperine; piperine derivatives; ethyl 2-(4-hydroxy-3-methoxy-phenyl)acetate and 3-phenylpropyl 2-(4-hydroxy-3-methoxy-phenyl)acetate and mixtures thereof.

The active substances perceived as pungent or acrid are preferably selected from the group consisting of aromatic isothiocyanates, in particular phenyl ethyl isothiocyanate, allyl isothiocyanate, cyclopropyl isothiocyanate, butyl isothiocyanate, 3-methylthiopropyl isothiocyanate, 4-hydroxybenzyl isothiocyanate, 4-methoxybenzyl isothiocyanate and mixtures thereof.

The tingling agents are preferably selected from the group consisting of 2E,4E-decadienoic acid-N-isobutylamide (trans-pellitorin), in particular those as described in WO 2004/043906; 2E,4Z-decadienoic acid-N-isobutylamide (cis-pellitorin), in particular those as described in WO 2004/000787; 2Z,4Z-decadienoic acid-N-isobutylamide; 2Z,4E-decadienoic acid-N-isobutylamide; 2E,4E-decadienoic acid-N-([2S]-2-methylbutyl)amide; 2E,4E-decadienoic acid-N-([2S]-2-methylbutyl)amide; 2E,4E-decadienoic acid-N-([2R]-2-methylbutylamide); 2E,4Z-decadienoic acid-N-(2-methylbutyl)amide; 2E,4E-decadienoic acid-N-piperide (achilleamide); 2E,4E-decadienoic acid-N-piperide (sarmentin); 2E-decenoic acid-N-isobutylamide; 3E-decenoic acid-N-isobutylamide; 3E-nonenoic acid-N-isobutylamide; 2E,6Z,8E-decatrienoic acid-N-isobutylamide (spilanthol); 2E,6Z,8E-decatrienoic acid-N-([2S]-2-methylbutyl)amide (homospilanthol); 2E,6Z,8E-decatrienoic acid-N-([2R]-2-methylbutyl)amide; 2E-decen-4-ynoic acid-N-isobutylamide; 2Z-decen-4-ynoic acid-N-isobutylamide; 2E,6Z,8E,10E-dodecatetraenoic acid-N-(2-methylpropyl)amide (alpha-sanshool); 2E,6Z,8E,10E-dodecatetraenoic acid-N-(2-hydroxy-2-methylpropyl)

amide (alpha-hydroxysanshool); 2E,6E,8E,10E-dodecatetraenoic acid-N-(2-hydroxy-2-methylpropyl)amide (gamma-hydroxysanshool); 2E,4E,8Z,10E, 12E-tetradecapentaenoic acid-N-(2-hydroxy-2-methylpropyl)amide (gamma-hydroxysanshool); 2E,4E,8E,10E, 12E-tetradecapentaenoic acid-N-(2-hydroxy-2-methylpropyl)amide (gamma-hydroxyisosanshool); 2E,4E,8Z,10E,12E-tetradecapentaenoic acid-N-(2-methyl-2-propenyl)amide (gamma-dehydrosanshool); 2E,4E,8Z,10E, 12E-tetradecapentaenoic acid-N-(2-methyl-propyl)amide (gamma-sanshool); 2E,4E,8Z,11Z-tetradecatetraenoic acid-N-(2-hydroxy-2-methylpropyl)amide (bungeanool); 2E,4E,8Z,11E-tetradecatetraenoic acid-N-(2-hydroxy-2-methylpropyl)amide (isobungeanool); 2E,4E, 8Z-tetradecatrienoic acid-N-(2-hydroxy-2-methylpropyl) amide (dihydrobungeanool) and 2E,4E-tetradecadienoic acid-N-(2-hydroxy-2-methylpropyl)amide (tetrahydrobungeanool) and mixtures thereof.

Active substances with astringent effect are preferably selected from the group consisting of: catechins, in particular epicatechins, gallocatechins, epigallocatechins and their respective gallic acid esters, in particular epigallocatechin gallate or epicatechin gallate, their oligomers (procyanidins, proanthocyanidins, prodelphinidins, procyanirins, thearubigenins, theogallins) and their C- and O-glycosides; dihydroflavonoids such as dihydromyricetin, taxifolin, and their C- and O-glycosides, flavonols such as myricetin, quercetin and their C- and O-glycosides such as quercetrin, rutin, gallic acid esters of carbohydrates such as tannin, pentagalloylglucose or their reaction products such as elligatannin, aluminium salts, e.g. alum, and mixtures thereof.

In a further variant of the method according to the invention, biogenic principles can also be encapsulated as core material, wherein the core material comprises at least one biogenic principle or mixtures thereof.

Biogenic principles are active substances with biological activity, for example tocopherol, tocopherol acetate, tocopherol palmitate, ascorbic acid, carnotine, carnosine, caffeine, (deoxy)ribonucleic acid and its fragmentation products, β-glucans, retinol, bisabolol, allantoin, phytantriol, panthenol, AHA acids, amino acids, ceramides, pseudoceramides, essential oils, plant extracts and vitamin complexes.

In a further variant of the process according to the invention, substances for print coatings for paper are also used as the active ingredient to be encapsulated or as the core material, as described in U.S. Pat. No. 2,800,457A, the disclosure of which is incorporated by reference in its entirety in the present description.

The content of lipophilic active ingredient or lipophilic active ingredient mixture for preparing the microcapsule according to the invention is 90.0 to 99.9% by weight, preferably 97.0 to 99.5% by weight, based on the total weight of the internal non-aqueous phase.

The ratio of the one or more active ingredient component (s) to the internal non-aqueous phase is preferably between 50:1 and 20:1, even more preferably between 40:1 and 30:1.

Thus, it is possible to achieve a high loading of the microcapsules of the invention with active ingredient using the method according to the invention.

Furthermore, the first polymerisation and/or cross-linking step (a) of the process according to the invention comprises providing an external aqueous phase comprising at least one protective colloid and optionally an emulsifier (a2).

For this purpose, the protective colloid and optionally the emulsifier are dissolved in the external aqueous phase, preferably an aqueous solvent. Suitable solvents are water or mixtures of water with at least one water-miscible organic solvent. Suitable organic solvents are for example glycerol, 1,2-propanediol, 1,3-propanediol, ethanediol, diethylene glycol, triethylene glycol and other analogues. Preferably, however, the solvent is water.

A protective colloid is a polymer system that prevents clumping (agglomeration, coagulation, flocculation) of the emulsified, suspended or dispersed components in suspension or dispersion. During solvation, protective colloids bind large amounts of water and generate high viscosities in aqueous solutions, depending on the concentration. During the production of oil-in-water emulsions, the protective colloid attaches itself to the primary particles with its hydrophobic part and turns its polar, i.e. hydrophilic, molecular part towards the aqueous phase. Through this attachment to the interface, it lowers the interfacial tension and prevents the agglomeration of the primary particles. In addition, it stabilises the emulsion and favours the formation of comparatively smaller droplets and thus also corresponding microcapsules.

In the process according to the invention, the protective colloid also exhibits emulsifying properties in addition to the above-mentioned properties. If the emulsifying properties of the protective colloid, such as carboxymethyl cellulose, acid-modified starch, polyvinyl alcohol, ammonium derivatives of polyvinyl alcohol, polystyrene sulphonates, polyvinyl pyrollidones, polyvinyl acrylates are sufficient, the use of an emulsifier in the downstream emulsification or dispersion step can thus advantageously be dispensed with in the process according to the invention.

The protective colloid used in the process according to the invention is selected from the group consisting of diols, in particular ethanediol, 1,2-propanediol, 1,3-propanediol, 1,2-butanediol, isomeric butanediol, 1,2-pentanediol, 1,2-hexanediol, 1,2-octanediol, 1,2-decanediol, 1,2-dodecanediol, and Polyols, preferably triols, in particular glycerol and its ethoxylation and propoxylation products, trimethylolpropane and its ethoxylation and propoxylation products, polyvinyl alcohol (PVOH) and its derivatives, in particular ammonium- or sulphonate-functionalised polyvinyl alcohols, polyphenols, preferably 1,3,5-trihydroxybenzene, polysaccharides, in particular glucose, starches or chemically, mechanically and/or enzymatically modified starches, cellulose derivatives such as hydroxyethylcellulose, in particular quaternised hydroxyethylcellulose, and carboxymethylcellulose, Polyvinylpyrrolidone, maleic acid vinyl copolymers, sodium lignosulphonates, maleic anhydride/styrene copolymers, ethylene/maleic anhydride copolymers, copolymers of ethylene oxide, propylene oxide and acid esters of polyethoxylated sorbitol, sodium dodecyl sulphate, animal and vegetable polymers, in particular gum arabic (Senegal type and Seyal type), proteins, gelatine, olibanum resin, shellac, lignin, chitosan, saponin as well as mixtures of the aforementioned compounds.

Preferably, the external aqueous phase comprises at least one protective colloid selected from polyvinylpyrrolidones, polyvinyl alcohols and mixtures thereof. Polyvinylpyrrolidones are particularly preferred. Commercial standard polyvinylpyrrolidones have molecular weights in the range of about 2500 to 750000 g/mol. Polyvinyl alcohol or its ammonium derivatives, 1,3,5-trihydroxybenzene or starches, in particular modified starches, or animal or vegetable polymers as protective colloid are/is particularly preferred for the production of the microcapsules according to the invention.

Starches, especially modified starches, or animal or plant polymers are naturally occurring substances that are biodegradable. In combination with the polyisocyanates described herein, the present process can thus provide biobased and biodegradable capsule shells. In the process according to the invention, the starch and the animal and plant polymers therefore also function as so-called bio-crosslinkers.

The starch used in the process according to the invention is selected from the group consisting of corn starch, potato starch, rye starch, wheat starch, barley starch, oat starch, rice starch, pea starch, tapioca starch and mixtures thereof.

The chemically modified starches are preferably acid-modified starches, alkali-modified starches, oxidised starches, acetylated starches, succinated starches or ocentylsuccinated starches.

According to the present invention, combinations of two or more different protective colloids can also be used to produce the microcapsule according to the invention.

It has proved to be particularly advantageous in the process according to the invention if a combination of one of the above-mentioned protective colloids with starch as a further protective colloid is used in the external aqueous phase. Such a combination stabilises the emulsion due to the high number of functional hydroxyl groups and, on the other hand, favours a reaction between the protective colloid and the polyisocyanate(s), whereby the reaction equilibrium in the reaction of the protective colloids with the polyisocyanate(s) is shifted to the side of the products, i.e. the polyurethanes. The large number of functional hydroxyl groups in starch also enables the formation of spatially particularly pronounced cross-links.

Depending on the number of functional groups and/or the size of the protective colloid, the above-mentioned protective colloids have different reaction rates with the isocyanate groups of the at least one polyisocyanate. For example, glycerol reacts faster with the isocyanate groups than, for example, starch due to its size. Therefore, the cross-linking of the protective colloid with the isocyanate groups of the polyisocyanate can be controlled by the selection of the protective colloid.

Glycerol with starch or with modified starch or the combination of glycerol with quaternised hydroxyethyl cellulose or gum arabic type Seyal has proven to be a particularly advantageous combination; with such a combination one makes use of the previously described properties of both protective colloids: high reaction rate of glycerol on the one hand and number of polymerisable functional groups of the other protective colloid on the other hand.

The protective colloids used in the process according to the invention have a dual function in that, on the one hand, they act as a protective colloid and thus prevent the agglomeration of the emulsified, suspended or dispersed components, stabilise the emulsion subsequently formed, promote the formation of small droplets and stabilise the microcapsule dispersion ultimately formed.

On the other hand, the protective colloid cross-links with the at least one or more polyisocyanate(s) under polymerisation due to properties capable of polymerisation, for example functional groups, in particular OH groups. Due to the cross-linking with the at least one polyisocyanate, a polymer layer is already formed during the emulsification step (a3), which contributes to the structure of the capsule wall and becomes a component thereof.

Surprisingly, it was found that already during emulsification or suspension of the internal non-aqueous phase in the external aqueous phase in the presence of the protective colloid, preferably a polyol, a polymerisation and/or cross-linking is formed near the core by interfacial polymerisation at the interfaces of the emulsified or suspended hydrophobic droplets of active substance to be encapsulated, which form the core of the microcapsule according to the invention, and the outer external phase. The polymerisation and/or cross-linking is based on the polyaddition reaction of the polyisocyanate with the protective colloid, preferably a polyol, to form a capsule shell or capsule wall of polyurethane according to the following formula:

$$n \; O\!=\!C\!=\!N\!-\!R^1\!-\!N\!=\!C\!=\!O + n \; HO\!-\!R^2\!-\!OH \longrightarrow$$
$$(\!-\!R^2\!-\!O\!-\!CO\!-\!NH\!-\!R^1\!-\!NH\!-\!CO\!-\!O\!-\!)_n$$

This is shown by gas evolution and release of carbon dioxide.

The formation of a polymer layer during the emulsification or dispersion step protects the active ingredient(s) to be encapsulated, in particular active ingredients with aldehyde, carboxylic acid or ester functionalities, are protected so that, if necessary, deprotonation, oxidation or saponification can be prevented or at least minimised, in particular in the subsequent process step, and a loss of lipophilic active ingredient(s) can be reduced or eliminated as a result; such degradation products usually also contribute to the instability of the emulsion.

The ratio of the amount of the protective colloid or colloids used to the aqueous phase according to the present invention is preferably in a range from 1:50 to 1:10, more preferably in a range from 1:40 to 1:30.

The ratio of protective colloid in the external aqueous phase to polyisocyanate in the internal non-aqueous phase is in a range from 1:5 to 1:2, preferably in a range from 1:2 to 1:1.

The amount of protective colloid used, or the amount of a combination of protective colloids used, is thus in a range from 1 to 8% by weight, preferably in a range from 2 to 4% by weight, even more preferably in a range from 3 to 4% by weight, based on the total weight of the external aqueous phase.

The at least one protective colloid may or may not be a component of the capsule shell. In particular, protective colloids with a higher reactivity, as described above, will react more rapidly or readily with the isocyanate groups of the polyisocyanate component and thus form polyurethane crosslinking units which are part of the capsule shell or capsule wall, in amounts of from 0.1 to a maximum of 15% by weight, but preferably in the range of from 1 to 5% by weight and even more preferably from 1.5 to 3% by weight, based on the weight of the capsules.

In order to facilitate the formation of an emulsion or dispersion of internal non-aqueous phase and external aqueous phase, to stabilise the formed emulsion or dispersion and to prevent segregation of the internal non-aqueous (oily/organic/hydrophobic) phase and the external aqueous (hydrophilic) phase, an emulsifier or emulsification aid is optionally added to the external aqueous phase in the process according to the invention. The addition of an emulsifier is optionally carried out when the protective colloid has no or only low, i.e. insufficient, emulsifying properties. If an emulsifying protective colloid is used, the use of an emulsifier can advantageously be dispensed with in the process according to the invention.

In the process according to the invention, O/W emulsifiers are preferably used as emulsifiers, which enable a homogeneous dispersion of the oil droplets of the internal non-aqueous phase in the external aqueous phase and stabilise the emulsion. The same applies to the mixing of solid, non-soluble active ingredients in the external aqueous phase in order to stabilise the dispersion thus obtained.

Suitable emulsifiers include, for example, non-ionic surfactants from at least one of the following groups:

Addition products of 2 to 30 moles of ethylene oxide and/or 0 to 5 moles of propylene oxide to linear fatty alcohols with 8 to 22 carbon atoms, to fatty acids with 12 to 22 carbon atoms, to alkylphenols with 8 to 15 carbon atoms in the alkyl group and to alkylamines with 8 to 22 carbon atoms in the alkyl group;

Alkyl and/or alkenyl oligoglycosides with 8 to 22 carbon atoms in the alk(en)yl radical and their ethoxylated analogues;

Addition products of 1 to 15 mol ethylene oxide to castor oil and/or hydrogenated castor oil;

Addition products of 15 to 60 mol ethylene oxide to castor oil and/or hydrogenated castor oil;

Partial esters of glycerol and/or sorbitan with unsaturated, linear or saturated, branched fatty acids with 12 to 22 carbon atoms and/or hydroxycarboxylic acids with 3 to 18 carbon atoms and their adducts with 1 to 30 moles of ethylene oxide;

Partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside) and polyglucosides (e.g. cellulose) with saturated and/or unsaturated, linear or branched fatty acids with 12 to 22 carbon atoms and/or hydroxycarboxylic acids with 3 to 18 carbon atoms as well as their adducts with 1 to 30 mol ethylene oxide, preferably Cremophor®;

Mixed esters of pentaerythritol, fatty acids, citric acid and fatty alcohol and/or mixed esters of fatty acids with 6 to 22 carbon atoms, methylglucose and polyols, preferably glycerol or polyglycerol;

Mono-, di- and trialkyl phosphates as well as mono-, di- and/or tri-PEG-alkyl phosphates and their salts;

Wool wax alcohols;

Polysiloxane-polyalkyl-polyether copolymers or corresponding derivatives; block copolymers, e.g. polyethylene glycol-30 dipolyhydroxystearates; polymer emulsifiers, e.g. Pemulen types (TR-1, TR-2) from Goodrich or Cosmedia® SP from Cognis;

Polyalkylene glycols and glycerine carbonate.

Typical anionic emulsifiers that can be used in the process of the invention for the production of the isocyanate-based microcapsules are aliphatic fatty acids with 12 to 22 carbon atoms, such as palmitic acid, stearic acid or behenic acid, as well as dicarboxylic acids with 12 to 22 carbon atoms, such as azelaic acid or sebacic acid.

Furthermore, zwitterionic surfactants can be used as emulsifiers in the process of the invention for the production of the isocyanate-based microcapsules. The term zwitterionic surfactants is used to describe surface-active compounds which have at least one quaternary ammonium group and at least one carboxylate and one sulphonate group in the molecule. Particularly suitable zwitterionic surfactants are the so-called betaines such as the N-alkyl-N, N-dimethylammonium glycinates, for example the cocoalkyl dimethylammonium glycinate, N-acylaminopropyl-N,N-dimethylammonium glycinate, for example the cocoacylaminopropyldimethylammoniumglycinate, and 2-alkyl-3-carboxylmethyl-3-hydroxyethylimidazolines each having 8 to 18 C atoms in the alkyl or acyl group as well as the cocoacylaminoethylhydroxyethylcarboxymethylglycinate. The fatty acid amide derivative known under the CTFA designation cocamidopropyl betaine is particularly preferred.

Ampholytic surfactants are also suitable emulsifiers. Ampholytic surfactants are surface-active compounds which, in addition to a C8/18 alkyl or acyl group in the molecule, contain at least one free amino group and at least one —COOH or —SO3H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Particularly preferred ampholytic surfactants are the N-cocoalkylaminopropionate, the cocoacylaminoethylaminopropionate and the C12/18-acylsarcosine.

Finally, cationic surfactants can also be considered as emulsifiers, with those of the esterquat type, preferably methyl-quaternised difatty acid triethanolamine ester salts, quaternised hydroxyethylcellulose, modified chitosan with propylene glycol and quaternised with epichlorohydrin, distearyldimethylammonium chloride (DSDMAC), benzalkonium chloride, benzethonium chloride, cetylalkonium chloride, cetylpyridinium chloride, cetyltrimethylammonium bromide (cetrimonium bromide), dequalinium chloride are particularly preferred.

The emulsifiers may be added to the external aqueous phase in an amount of from about 0.5% to about 10% by weight, and preferably from about 1% to about 5% by weight, each based on the total weight of the external aqueous phase.

The aqueous protective colloid-emulsifier solution is preferably prepared with stirring by adding the protective colloid and optionally the emulsifier successively to the external aqueous phase or vice versa, or by adding the protective colloid and optionally the emulsifier simultaneously to the external aqueous phase.

It may be advantageous if, for the preparation of the polyurea/polyurethane microcapsules according to the present invention, the external aqueous phase optionally contains stabilisers either dissolved or dispersed to prevent segregation of the internal non-aqueous (oily) phase and the external aqueous phase.

The preferred stabilisers for the production of the isocyanate-based microcapsules according to the present invention are mainly acrylic copolymers which have sulphonate groups. Also suitable are copolymers of acrylamides and acrylic acid, copolymers of alkyl acrylates and N-vinylpyrrolidone, such as LUVISKOL® K15, K30 or K90 (BASF); sodium polycarboxylates, sodium polystyrene sulphonates, vinyl and methyl vinyl ether-maleic anhydride copolymers as well as ethylene, isobutylene or styrene-maleic anhydride copolymers, microcrystalline cellulose, which is commercially available, for example, under the name VIVAPUR®, diutan gum, xanthan gum or carboxymethyl celluloses.

The quantity of used stabilisers can be in the range of 0.01 to 10% by weight and in particular in the range of 0.1 to 3% by weight, in each case relative to the external aqueous phase.

Before mixing the internal non-aqueous phase and the external aqueous phase or before emulsifying/dispersing the internal non-aqueous phase in the external aqueous phase, the pH of the external aqueous phase is adjusted to an acidic pH in the range of 1 to 5. Preferably, the pH of the external aqueous phase is adjusted to a pH in the range of 3 to 5.

The pH value of the external aqueous phase is adjusted by adding an organic acid. Formic acid or acetic acid are most preferably used to adjust the pH value.

The oil-in-water emulsion is prepared by mixing the internal non-aqueous phase and the external aqueous phase. The weight ratio of internal non-aqueous phase to external aqueous phase is preferably in a range of 2:1 to 1:10, more preferably in a range of 1:2 to 1:4.

Emulsion formation in the case of liquid active ingredients or dispersion formation in the case of solid active ingredients, i.e. emulsification or dispersion of the internal non-aqueous or oily phase in the external aqueous or hydrophilic phase, takes place under high turbulence or strong shear. The diameter of the microcapsules obtained can be determined by the strength of the turbulence or shear. The droplet size can be checked by light scattering measurements or microscopy. The production of the microcapsules can be continuous or discontinuous. With increasing viscosity of the aqueous phase or with decreasing viscosity of the oily phase, the size of the resulting capsules usually decreases.

The process according to the invention for the production of the polyurea/polyurethane microcapsules can be carried out, for example, via a forced metering pump according to the "inline" technique or also in conventional dispersion apparatus or emulsification apparatus with stirring.

The emulsification or dispersion of the internal non-aqueous phase in the external aqueous phase was carried out for the production of microcapsules according to the invention by means of an emulsification turbine (IKA Eurostar 20 high-speed stirrer). The process of emulsification in step (a3) of the process according to the invention is advantageously carried out for a time of from 30 seconds to 20 minutes, preferably from 1 to 4 minutes, at a stirring speed of from 1000 rpm to 5000 rpm, preferably at 3000 rpm to 4000 rpm.

After completion of the emulsification or dispersion step (a3), an oil-in-water emulsion or dispersion is present in which the internal oily phase with the active ingredients to be encapsulated is finely emulsified or dispersed in the external aqueous phase in the form of droplets.

In a subsequent step (a4) of the process according to the invention, a first polymerisation and/or crosslinking of the material of the capsule shell or capsule wall is also carried out with stirring. The first cross-linking is carried out by adding at least one first amino acid or at least one amino acid hydrochloride, preferably in the form of an aqueous solution, in the presence of a catalyst. The addition of the amino acid or amino acid hydrochloride and the catalyst is preferably carried out at a temperature of 20 to 30° C.

The at least one first amino acid is selected from the group consisting of arginine, histidine, lysine, tryptophan, ornithine and mixtures thereof.

It is often advantageous to use the amino acid as a hydrochloride. The hydrochlorides of the aforementioned amino acids are more easily soluble in water and thus more easily soluble in the external aqueous phase. Furthermore, the use of the amino acid as a hydrochloride shifts the pH of the reaction mixture to acidic, whereby, in addition to improved solubility, increased reactivity between the at least one polyisocyanate and the first amino acid, and thus increased polymerisation and/or cross-linking between these two components, can be expected.

The at least one amino acid hydrochloride is selected from the group consisting of arginine hydrochloride, histidine hydrochloride, lysine hydrochloride, tryptophan hydrochloride, ornithine hydrochloride, and mixtures thereof.

The amino acids arginine, lysine and ornithine or the corresponding amino acid hydrochlorides are compounds with two amino groups in the side chain. The amino acids histidine and tryptophan or the corresponding hydrochlorides each have one amino group and one NH functionality in the side chain. The aforementioned amino acids or their amino acid hydrochlorides thus exhibit multifunctionality for polymerisation with the at least one polyisocyanate.

Due to the cross-linking between the functional groups of the at least one polyisocyanate and the at least one amino acid or amino acid hydrochloride, first cross-linking units or a first cross-linking matrix are formed which become part of the capsule shell or capsule wall.

Of the aforementioned amino acids, the basic-reacting amino acid arginine or its hydrochloride analogue is particularly preferred as a crosslinking agent because of its water solubility, high reactivity and pH, both as an amino acid and as a hydrochloride.

The use of amino acids or amino acid hydrochlorides as cross-linking agents is particularly advantageous from an environmental point of view with regard to biodegradability and biocompatibility.

The amino acid or amino acid hydrochloride, i.e. the first cross-linking agent, is added to the emulsion or dispersion either as such, for example as a solid, or preferably in the form of an aqueous solution. The amino acid or amino acid hydrochloride is present in the aqueous solution in a concentration of 0.5 to 2 mol/l, preferably 1 mol/l.

The amount of the at least one amino acid or the at least one amino acid hydrochloride is adjusted such that 1 to 3 moles of amino groups, preferably 1 to 2 moles of amino groups, are added for each mole of isocyanate group.

No specific action is required to induce polymerisation between the at least one polyisocyanate or the plurality of polyisocyanates and the first amino acid or amino acid hydrochloride. The reaction starts immediately after addition of the amino acid or amino acid hydrochloride to the oil-in-water emulsion or dispersion, forming first crosslinking units or a first crosslinking matrix. Since the reaction between the at least one polyisocyanate or the plurality of polyisocyanates and the first amino acid or amino acid hydrochloride is fast enough, it does not require a catalyst.

To optimise the polymerisation or cross-linking between the functional groups of the at least one polyisocyanate or the several polyisocyanates and the first amino acid or the amino acid hydrochloride, the pH of the emulsion or dispersion is adjusted to a pH in the range of 4 to 8 at the beginning of the reaction. Preferably, the pH of the emulsion or dispersion is adjusted to a pH in the range of 6 to 8.

The pH of the emulsion or dispersion is adjusted by adding an aqueous alkaline solution. Most preferably, sodium hydroxide or potassium hydroxide is used to adjust the pH.

The formation of the first cross-linking units in the process according to the invention is based on the polyaddition reaction of the polyisocyanate or polyisocyanates with the amino acid or amino acid hydrochloride. The first cross-linking units forming the capsule shell or capsule wall are based on a polyurea structure. The polyurea linkage or polyurea structure is formed by polyaddition of the amino group(s) ($-NH_2$) of the at least one amino acid or the at least one amino acid hydrochloride to the isocyanate group of the at least one polyisocyanate:

$$n \ O{=}C{=}N{-}R^1{-}N{=}C{=}O{+}n \ H_2N{-}R^2{-}{\rightarrow}({-}$$
$$O{-}NH{-}R^1{-}NH{-}CO{-}NH{-}R^2{-})_n$$

In the process according to the invention, a first crosslinking matrix or first crosslinking units, in particular polyurea crosslinking units, for the construction of a capsule shell or capsule wall is formed by interfacial polymerisation at the interface of the emulsified or dispersed oil droplets which enclose the lipophilic active substance to be encapsulated.

By forming the first cross-linking matrix or first cross-linking units, the emulsified or dispersed oil droplets with the core material, i.e. the encapsulated active ingredients, are enclosed by the cross-linking matrix or cross-linking units on the outside at the interface, thus generating a capsule wall, which makes diffusion of the encapsulated active ingredient more difficult.

The addition of at least a first catalyst to the emulsion or dispersion accelerates the reaction between polyisocyanates and the amino acid or amino acid hydrochloride and catalyses the reaction in favour of the formation of a polyurea crosslinking matrix.

The catalyst added in the process according to the invention is preferably diazabicyclo[2.2.2]octane (DABCO), also called triethylenediamine (TEDA), a bicyclic tertiary amine. DABCO is generally used as a catalyst for the production of polyurethane plastics. The tertiary amine with free electron pairs promotes the reaction between the at least one polymerisable polyisocyanate and the amino groups of the first amino acid or the amino acid hydrochloride.

In addition to DABCO, catalysts based on bismuth or tin, for example, are also used for catalysis of the first crosslinking, such as catalysts based on bismuth(II) salts or bismuth(III) salts, as described in K. C. Frisch & L. P. Rumao, Catalysis in Isocyanate Reactions, Polymer Reviews, 1970, 5:1, pages 103-149, DOI: 10.1080/15583727008085365, the disclosure of which is incorporated herein by reference in its entirety.

Diazabicyclo[2.2.2]octane (DABCO) is particularly preferred as a catalyst.

According to the invention, a combination of DABCO and one of the above-mentioned catalysts is preferred. Such a mixture leads to a multiplication of reactivity as described in K. C. Frisch & L. P. Rumao, Catalysis in Isocyanate Reactions, Polymer Reviews, 1970, 5:1, pages 103-149, DOI: 10.1080/15583727008085365, the disclosure of which is incorporated herein in its entirety.

In the process according to the invention, DABCO and the aforementioned catalysts preferably catalyse the polyurethane reaction between the at least one polymerisable polyisocyanate with two or more isocyanate groups and the diols or polyols.

The amount in which the catalyst is added to the emulsion or dispersion is in a range of 0.01 to 1% by weight and preferably in a range of 0.05 to 0.2% by weight, based on the total weight of the emulsion or suspension. In case of a sluggish polymerisation reaction, the required amount of catalyst can be adjusted accordingly.

The ratio of catalyst in the emulsion or dispersion to the at least one polyisocyanate in the internal non-aqueous phase preferably in a range from 1:20 to 1:50.

It has been shown to be advantageous that the catalyst is first dispersed or dissolved in water and then added to the emulsion or dispersion with stirring.

The addition of the first amino acid or the amino acid hydrochloride and the catalyst is preferably carried out at a stirring speed of 500 rpm to 2000 rpm, particularly preferably at 1000 rpm to 1500 rpm and at temperatures of 20° C. to 30° C., preferably at temperatures of 22° C. to 26° C.

The first polymerisation and/or cross-linking in the process according to the invention is carried out for a period of time of about 10 minutes to 20 minutes, preferably for a period of time of 12 to 18 minutes and most preferably for a period of time of about 15 minutes.

Surprisingly, the addition of the catalyst after the emulsification or dispersion step leads to a significant increase in capsule stability. Capsules produced in this way show a significantly higher stability, even after 10 days at 50° C., and a significant reduction in free perfume oil with respect to comparative capsules produced without the addition of a catalyst.

Particularly stable capsules could be produced with the catalyst diazabicyclo[2.2.2]octane (DABCO).

The first polymerisation and/or crosslinking step (a) in the process according to the invention is followed by a further, i.e. second, polymerisation and/or crosslinking step (b) by adding at least one hydroxyl group donor to the oil-in-water emulsion or dispersion obtained in process step (a4) in order to further build up the capsule shell or capsule wall.

The at least one hydroxyl group donor is preferably a polyol having two or more hydroxyl functional groups, with good to very good water solubility at temperatures above 40° C.

The hydroxyl group donor is selected from the group consisting of glycerol, propylene glycol, 1,3,5-trihydroxybenzene, starches, modified starches, cellulose derivatives such as hydroxyethylcellulose, in particular quaternised hydroxyethylcellulose, or carboxymethylcellulose, gum arabic (Senegal type and Seyal type) and mixtures thereof. Glycerol and starch are preferred; glycerol is the most preferred.

The starch used in the process according to the invention is selected from the group consisting of corn starch, potato starch, rye starch, wheat starch, barley starch, oat starch, rice starch, pea starch, tapioca starch and mixtures thereof.

The modified starches are preferably chemically modified starches, namely acid modified starches, alkali modified starches, oxidised starches, acetylated starches, succinated starches or ocentylsuccinated starches.

According to the present invention, a combination of two different ones of the above-mentioned hydroxyl group donors can also be used to produce the microcapsule according to the invention.

Depending on their size, the above-mentioned hydroxyl group donors have different reaction rates with the isocyanate groups of the at least one polyisocyanate. For example, glycerol reacts faster with the isocyanate groups than starch, for example, due to its size.

A particularly advantageous combination has therefore proved to be glycerol with starch or modified starch or the combination of glycerol with quaternised hydroxyethyl cellulose or gum arabic type Seyal; with such combinations one makes use of the previously described properties of both hydroxyl group donors: high reaction rate of glycerol on the one hand and number of polymerisable functional groups of starch on the other.

Through the reaction of the at least one polyisocyanate and/or isothiocyanate with the hydroxyl groups of the hydroxyl group donor, a further, i.e. second, crosslinking matrix or second crosslinking units are formed for the construction or formation of the capsule shell or capsule wall, the structure of which can be derived analogously to the polyurethane crosslinking units from polyisocyanates and protective colloid, as described above.

The polyaddition reaction of the at least one polyisocyanate with the hydroxyl group donor, results in the formation of so-called urethane bridges (—NH—CO—C—) by addition of the hydroxyl groups of the hydroxyl group donor (—OH) to the carbon atom of the carbon-nitrogen bond of the polyisocyanate groups (—N═C═O).

By forming such further polyurethane crosslinking units, the first polyurea crosslinking units formed in the first polymerisation and/or crosslinking step (a4) are further crosslinked and densified.

In order to obtain particularly efficient, dense and stable cross-links, the second polymerisation and/or cross-linking step (b) with the hydroxyl group donor is carried out at temperatures between 40° C. and 60° C., and preferably at temperatures between 45° C. and 55° C. even more preferably at temperatures between 45° C. and 50° C.

Furthermore, it is preferred that the step of further crosslinking is carried out by adding the hydroxyl group donor at stirring speeds of from 900 rpm to 1700 rpm, preferably from 1000 rpm to 1300 rpm.

In this context, it has been found that adding the hydroxyl group donor in aqueous form leads to particularly stable crosslinkings and therefore particularly stable capsule shells or capsule walls. The concentration of the hydroxyl group donor in the aqueous solution is preferably 10% to 70% and even more preferably the concentration of the hydroxyl group donor in the aqueous solution is 40% to 60%.

The second polymerisation and/or cross-linking step (b) in the process according to the invention is followed by a further, i.e. third, polymerisation and/or cross-linking step (c). In this third cross-linking step, at least one further, i.e. a second, amino acid is added as cross-linking agent to the oil-in-water emulsion obtained in cross-linking step (b).

The at least one second amino acid is selected from the group consisting of arginine, histidine, aspartic acid, lysine, glycine, alanine, proline, cysteine, glutamine, leucine, serine, tryptophan, valine, threonine, ornithine, uric acid, and mixtures thereof.

The aforementioned amino acids are compounds with at least one amino group in the side chain and thus exhibit functionality for polymerisation and/or crosslinking with the at least one polyisocyanate.

Of the aforementioned amino acids, the basic-reacting amino acids such as arginine, histidine, lysine or their hydrochloride analogues are particularly preferred due to their high reactivity and pH values both as amino acid and hydrochloride.

Arginine is particularly preferred as a crosslinking agent in the process according to the invention because of its solubility in water.

The use of amino acids or amino acid hydrochlorides as cross-linking agents is particularly advantageous from an environmental point of view with regard to biodegradability and biocompatibility.

The second amino acid or amino acid hydrochloride is added to the emulsion either as such, for example as a solid, or preferably in the form of an aqueous solution. The amino acid or amino acid hydrochloride is present in the aqueous solution in a concentration of 0.5 to 2 mol/l, preferably 1 mol/l.

The amount of the at least one second amino acid or amino acid hydrochloride is typically adjusted such that 1 to 3 moles of amino groups, preferably 1 to 2 moles of amino groups, are added for each mole of isocyanate group.

To optimise polymerisation or cross-linking between the functional groups of the at least one polyisocyanate or the plurality of polyisocyanates and the second amino acid or amino acid hydrochloride, the pH of the emulsion or dispersion is adjusted to a pH in the range of 4 to 8 at the beginning of the reaction. Preferably, the pH of the emulsion or dispersion is adjusted to a pH in the range of 6 to 8.

The pH of the emulsion or dispersion is adjusted by adding an aqueous alkaline solution. Most preferably, sodium hydroxide or potassium hydroxide is used to adjust the pH.

By adding a second amino acid in the presence of the catalyst described above, a third cross-linking matrix or third cross-linking units are formed in the process according to the invention to build up the capsule shell or capsule wall. These third cross-linking units are based on the polyaddition reaction of individual polymers or oligomers of the polyisocyanate or polyisocyanates with the amino acid to form a capsule shell or capsule wall based on a polyurea structure. The formation of the polyurea linkage or polyurea structure is achieved by polyaddition of the amino group(s) ($-NH_2$) of the at least one amino acid to the isocyanate group of the at least one polyisocyanate:

$$n\ O=C=N-R^1-N=C=O+n\ H^2N-R^2-+\rightarrow(-O-NH-R^1-NH-CO-NH-R^2-)_n$$

By forming such further polyurea crosslinking units, the polyurea crosslinking units and polyurethane crosslinking units formed in the first and second polymerisation and/or crosslinking steps (a4) and (b) are further crosslinked and densified.

The addition of the second amino acid or amino acid hydrochloride is preferably carried out at a stirring speed of 500 rpm to 2000 rpm, more preferably at 1000 rpm to 1500 rpm and at a temperature of 60 to 80° C., preferably of 60° C.

The third cross-linking in the process according to the invention is carried out for a period of about 10 minutes to 20 minutes, preferably for a period of about 12 to 18 minutes and most preferably for a period of about 15 minutes.

In order to obtain a particularly efficient, dense and stable network of the capsule wall components, a further, i.e. second, catalyst can optionally be added to the emulsion or dispersion in a further step (d).

The further catalyst added in the process according to the invention is preferably para-toluenesulfonic acid, sulphuric acid, germanium oxide or enzymatic catalysts, preferably Candida antarctica lipase B (CALB). These catalysts are preferably catalysts that favour ester reactions.

The addition of a further catalyst to the emulsion or dispersion preferably accelerates ester reactions, i.e. the formation of polyester, from cross-links of protective colloid, hydroxyl group donor and release agent and further catalyses the reaction in favour of the formation of a three-dimensional, dense and stable polyurea and/or polyurethane and/or polyester cross-link matrix.

The amount of catalyst added to the emulsion or dispersion is in the range of 0.01 to 1% by weight and preferably in the range of 0.05 to 0.2% by weight, based on the total weight of the emulsion or dispersion. In case of a slower polymerisation reaction, the required amount of catalyst can be adjusted accordingly.

The ratio of catalyst in the emulsion or dispersion to the at least one polyisocyanate in the internal non-aqueous phase preferably in a range from 1:20 to 1:50.

It has been shown to be advantageous that the catalyst is first dispersed or dissolved in water and then added to the emulsion or dispersion with stirring.

The addition of the further catalyst is preferably carried out at a stirring speed of 500 rpm to 2000 rpm, more preferably at 1000 rpm to 1500 rpm and at temperatures of 20° C. to 30° C., preferably at temperatures of 22° C. to 26° C. The cross-linking promoted or accelerated by the further catalyst in the process according to the invention is carried out for a period of about 10 minutes to 20 minutes, preferably for a period of 12 to 18 minutes and most preferably for a period of about 15 minutes.

The combination of a first polymerisation or cross-linking step between polyisocyanate and a first amino acid, a second polymerisation or cross-linking step between polyisocyanate and hydroxyl group donor, and a third polymerisation or cross-linking step between polyisocyanate and a second amino acid allows polyurea and polyurethane cross-linking units or cross-linking matrices to be generated which build up the capsule shell or capsule wall. The first, second and third polyurea and polyurethane cross-linking units are further spatially cross-linked to each other and among each other by the sequential cross-linking steps in the method of the invention. Through the optional combination with a further catalyst, in addition to the above-mentioned polyurea and polyurethane cross-linking units, polyester cross-links are also generated, which furthermore lead to further cross-linking and thus to the construction of a three-dimensional, dense and stable capsule shell or capsule wall of the microcapsule.

The higher the number of cross-linking functional groups, the greater the spatial cross-linking and the denser and more stable the resulting capsule shell or capsule wall of the microcapsule. In addition to the number of functional groups, the chain length of the individual building blocks significantly influences the mechanical properties, i.e. the stability, of the capsules. For example, the large number of hydroxyl groups in starch enables the formation of spatially particularly pronounced cross-links. Longer-chain capsule shell or capsule wall building blocks, such as polyisocyanates, lead to the formation of more stable capsule shells or capsule walls.

During the cross-linking steps described above, the stirring power is reduced, preferably to a stirring speed of about 800 to 1200 rpm, in order not to immediately break up the cross-linking units forming the capsule shell.

After the third polymerisation or cross-linking step and the complete cross-linking and formation of the capsule shell or capsule wall, the capsules produced according to the process of the invention are present as crude microcapsules in the form of an aqueous dispersion or a slurry.

After cross-linking, the microcapsules in the slurry still have a flexible shell that is not particularly stable and therefore breaks open easily. For this purpose, the shell of the microcapsules is cured. The curing is preferably carried out by gradually raising the microcapsule dispersion to a temperature of at least 60° C., preferably to a temperature in the range of 60 to 65° C., up to a maximum of the boiling point of the microcapsule dispersion. The curing is usually carried out over a period of at least 60 minutes, preferably 2 to 4 hours.

In addition, it is advantageous to add substances to the external aqueous phase for curing. For this purpose, natural plant tannins of the tannin type are used, which, from a chemical point of view, are proanthocyanidins as found in dicotyledonous shrubs, bushes and leaves, especially in the tropics and subtropics. The terpenes usually have molecular weights in the range of 500 to 3000 KDa. A preferred example of a suitable tannin is corigallin. For curing, an aqueous preparation of the tannins is added to the aqueous dispersion containing the crude microcapsules. Typically, the tannins are added in amounts of from about 0.1 to about 2% by weight and preferably from about 0.5 to about 1.5% by weight, based on the microcapsules.

After the curing step (e) of the process according to the invention, at least one release agent is added to the microcapsule dispersion or microcapsule slurry in a further process step (f), which is drawn onto the microcapsule shell or microcapsule wall or is preferably incorporated into the microcapsule shell or microcapsule wall.

The release agent is conventionally a liquid or paste-like substance that prevents adhesion between two materials. In the case of the present invention, these are substances that are incorporated into the microcapsule shell or microcapsule wall and form ionic or even covalent bonds with the existing crosslinking structures of the capsule material via functional groups, for example OH groups or COOH groups.

The at least one release agent used in the process according to the invention is selected from the group consisting of fatty acids, fatty alcohols, fatty acid esters and animal and vegetable waxes.

Fatty acids are aliphatic monocarboxylic acids with mostly unbranched carbon chains. Fatty acids differ in the number of carbon atoms (chain length) and—in the case of unsaturated fatty acids—in the number and position of double bonds. Based on their chain lengths, fatty acids can be divided into short-chain fatty acids (up to 6 to 8 C atoms), medium-chain fatty acids (8 to 12 C atoms) and long-chain fatty acids (13 to 21 C atoms).

Fatty alcohols are aliphatic, long-chain, monovalent, mostly primary alcohols. The hydrocarbon residues are often unbranched in native fatty alcohols, synthetic fatty alcohols are often also branched. The carbon chain has 6 to 30 carbon atoms and can also be mono- or polyunsaturated. Fatty alcohols are found in natural waxes, bound as carboxylic acid esters, e.g. in wool wax or spermaceti, and are often called wax alcohols.

Wax is an organic compound that melts at above about 40° C. and then forms a liquid of low viscosity. Waxes can vary greatly in their chemical composition and origin. The main components of these mixtures are esters of fatty acids with long-chain, aliphatic primary alcohols, the so-called fatty alcohols. These esters differ in their structure from fats and fatty oils, which are triglycerides with fatty acids. In addition, these waxes also contain free, long-chain, aliphatic carboxylic acids, ketones, alcohols and hydrocarbons. The waxes can be of animal or plant origin.

The at least one release agent in the process according to the invention is preferably selected from the group consisting of:

long-chain, aliphatic, linear or branched, saturated or unsaturated carboxylic acids with 12 to 30 C atoms (fatty acids), in particular lauric acid (12:0), tridecanoic acid (13:0), myristic acid (14:0), pentadecanoic acid (15:0), palmitic acid (16:0), margaric acid (17:0), stearic acid (18:0), nonadecanoic acid (19:0), arachidic acid (20:0), heneicosanoic acid (21:0), behenic acid (22:0), lignoceric acid (24:0), cerotinic acid (26:0), montanic acid (28:0) and melissic acid (30:0); myristoleic acid (14:1), palmitolic acid (16:1), margaroleic acid (17:1), petroselinic acid (18:1), oleic acid (18:1), elaidic acid (18:1), vaccenic acid (18:1), gadoleic acid (20:1), gondoic acid (20:1), cetoleic acid (22:1), erucic acid 822:1), nervonic acid (24:1), Linoleic acid (18:2), alpha-linolenic acid (18:3), gamma-linolenic acid (18:3), calendulic acid (18:3), punicic acid (18:3), alpha-eloeostearic acid (18:3), beta-eloeostearic acid (18:3), stearidonic acid (18:4), arachidonic acid (20:4), eicosapentaenoic acid (20:5), docosatetraenoic acid (ADA) (22:4), docosapentaenoic acid (DPA-3) (22:5), docosahexaenoic acid (22:6) and tetracosahexaenoic acid (24:6); phytanic acid;

long-chain, aliphatic, linear or branched, saturated or unsaturated primary alcohols with 12 to 30 C atoms (fatty alcohols), in particular lauryl alcohol (12:0), myristyl alcohol (14:0), palmityl alcohol (16:0), margaryl alcohol (17:0), stearyl alcohol (18:0), arachidyl alcohol (20:0) behenyl alcohol (22:0), lignoceryl alcohol (24:0), ceryl alcohol (26:0), montanyl alcohol (28:0) and melissyl alcohol (30:0); palmitoleyl alcohol (16:1), oleyl alcohol (18:1), elaedyl alcohol (18:1), linoleyl alcohol (18:2), gamma-linolenyl alcohol (18:3);

esters of long-chain, aliphatic saturated carboxylic acids with 12 to 30 C atoms with long-chain, aliphatic primary alcohols with 12 to 30 C atoms, in particular lauryl palmitate, myricyl palmitate, cetylarachinate and stearyl behenate;

animal and vegetable waxes, in particular wool wax, China wax, beeswax, sunflower seed wax, rice bran wax, carnauba wax, pinova wax, rapeseed wax, soy wax, candelilla wax, jojoba oil, cork wax, guaruma wax, cotton wax, flax wax, peat wax, rose wax, jasmine wax, peetha wax from wash gourd, as well as myrtle wax (*Myrica* cerifera), wax fig wax, berry wax, and mixtures of two or more of the above release agents.

Of the carboxylic acids listed above, the saturated fatty acids are preferred. Most preferred in the process according to the invention is the use of the animal and vegetable waxes specified above due to their lower melting points, which facilitate incorporation into the microcapsule shell or microcapsule wall.

The at least one release agent has a dual functionality: The incorporation of the release agent into the microcapsule shell or microcapsule wall and the formation of ionic or covalent bonds of the release agent with the crosslinking units or crosslinking matrices causes, on the one hand, a further stabilisation of the microcapsule shell. On the other hand, the incorporation of the release agent into the microcapsule shell or microcapsule wall generates predetermined breaking points for the degradability of the microcapsule shell, i.e. points in the microcapsule wall which are designed in such a way that degradation of the microcapsule material takes place there first. This facilitates the degradation of the microcapsule shell or microcapsule wall. The use of a release agent that stabilises the microcapsule shell or microcapsule wall also makes it possible to reduce other capsule wall materials that are less biodegradable or not biodegradable at all.

The release agent is added to the microcapsule dispersion or microcapsule slurry in an amount of 1 to 10% by weight, based on the capsule shell. Preferably, the release agent is added in an amount of 2 to 5% by weight, based on the capsule shell.

The at least one release agent is added to the microcapsule dispersion or microcapsule slurry from process step (e) at a temperature of at least 60° C. up to a maximum of the boiling point of the microcapsule dispersion, preferably at a temperature of 80° C. At this temperature, the release agent is in a liquid or molten form so that it can be easily melted into and incorporated into the existing cross-linking structures of the microcapsule shell.

After the addition of the at least one release agent, a step of post-curing the polyurea/polyurethane microcapsules obtained in step (g) is carried out, preferably at a temperature of at least 60° C. to 100° C. and for a period of time of 60 to 240 minutes.

After curing, the microcapsules produced according to the process of the invention are present as a dispersion in water, which is also called microcapsule dispersion or microcapsule slurry. In this form, the microcapsules are basically already marketable.

In order to prevent segregation or creaming of such a suspension and thus to achieve a high storage stability, it has proven advantageous that the suspension has a viscosity of 12 to 1500 mPas. To obtain the desired viscosity of the suspension, a thickening agent is preferably used.

Xanthan gum, diuthan gum; carboxymethyl cellulose (CMC), microcrystalline cellulose (MCC) or guar gum are preferably used as thickening agents.

To improve shelf life, one or more preservatives are optionally added to the microcapsule slurry or the microcapsule slurry is dried.

Preferably 1,2-hexanediol, 1,2-octanediol or parmetol are used as preservatives.

Alternatively, the microcapsules are separated and dried for preservation purposes.

In principle, processes such as lyophilisation can be used for this, but spray drying, for example in the fluidised bed, is preferred. It has proven advantageous to add further polysaccharides, preferably dextrins and in particular maltodextrins, to the dispersion at temperatures of about 20 to about 50° C. and preferably about 40° C., which support the drying process and protect the capsules during this process. The amount of polysaccharides used in the dispersion may be from about 50 to about 150% by weight and preferably from about 80 to about 120% by weight, based on the capsule mass.

The spray drying itself can be carried out continuously or in batches in conventional spray systems, with an inlet temperature of about 170 to about 200° C. and preferably about 180 to 185° C. and an outlet temperature of about 70 to about 80° C. and preferably about 72 to 78° C.

An important criterion for the usability of microcapsules is the weight ratio of core material to capsule wall material. While on the one hand the aim is to have the highest possible proportion of core material to enable the capsules to be as useful as possible, on the other hand it is necessary for the capsule to still have a sufficient proportion of capsule wall material to ensure the capsules' stability.

According to the invention, it has been shown to be particularly advantageous that the microcapsules are designed to have a weight ratio of core material to capsule wall material of 50:50 to 90:10, preferably 70:30 to 80:20.

The microcapsules produced by the process according to the invention can be characterised by the d(0.5) value of their size distribution, i.e. 50% of the capsules produced are larger, 50% of the capsules are smaller than this value.

The microcapsules according to the invention were prepared from hexamethylene diisocyanate and 4,4'-methyldiphenylene diisocyanate in a ratio of 75:25. Furthermore, lysine*HCl was used as the first amino acid, glycerol as the hydroxyl group donor and arginine as the second amino acid. DABCO was used as catalyst and a modified starch as protective colloid; beeswax was added as separating agent. The pH value of the aqueous phase before the emulsification step and the pH value of the emulsion or dispersion at the beginning of the reaction was adjusted to 5.5 in each case.

To determine the particle size, the microcapsules according to the invention are dispersed in water as part of a dynamic process and the particle size is then determined by means of laser diffraction. Depending on the size of the capsule, the laser beam is refracted differently and can thus be converted to a size. The Mie theory was used for this. A MALVERN Mastersizer 3000 was used for the particle measurement.

Figure 2:
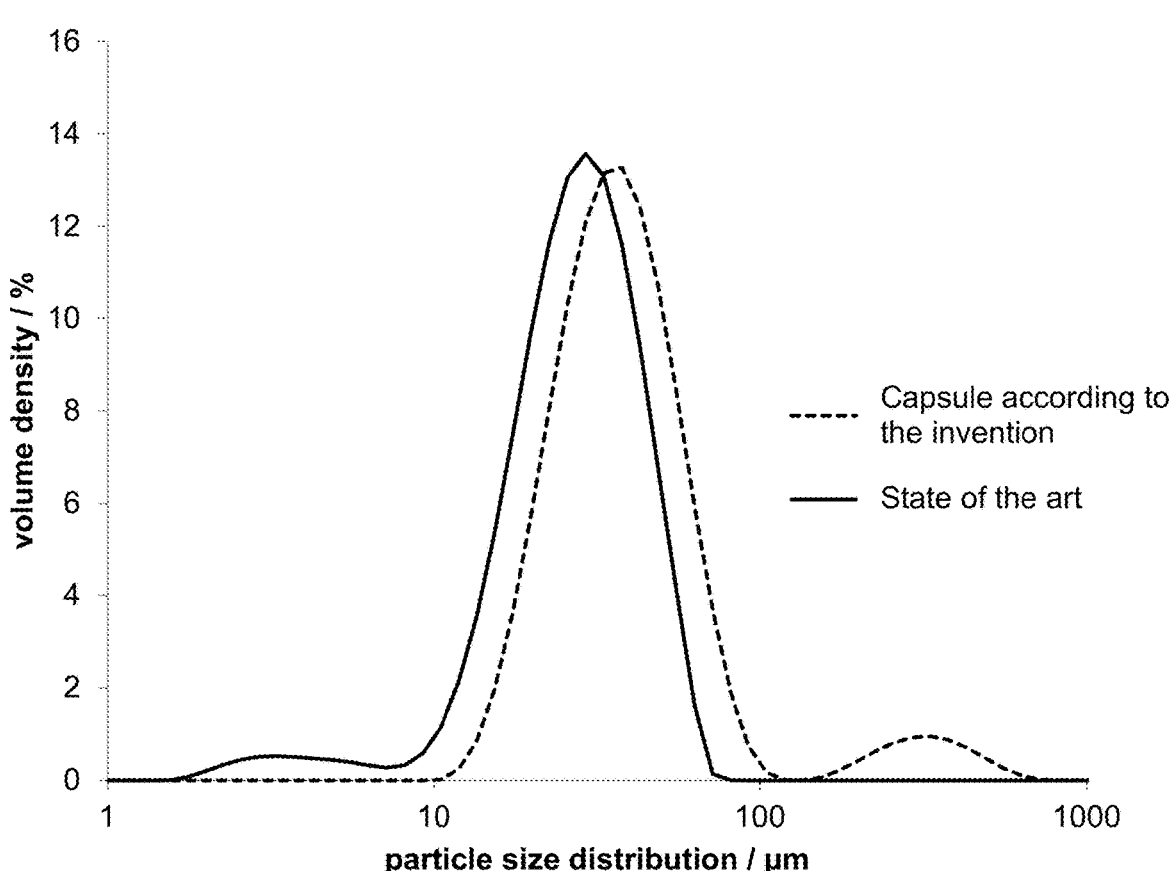

The microcapsules according to the invention are characterised in that they have a particle size distribution at a d(0.5) value of 10 μm to 100 μm, preferably a d(0.5) value of 20 μm to 65 μm. The corresponding particle size distributions of microcapsules according to the invention and microcapsules of the prior art are illustrated in FIG. 2.

The direct comparison of the microcapsules shows that microcapsules with the same particle size distribution as prior art microcapsules based on polyurea/polyurethane structures without release agents produced at a pH of 9 can be obtained with the method according to the invention.

Figure 3:
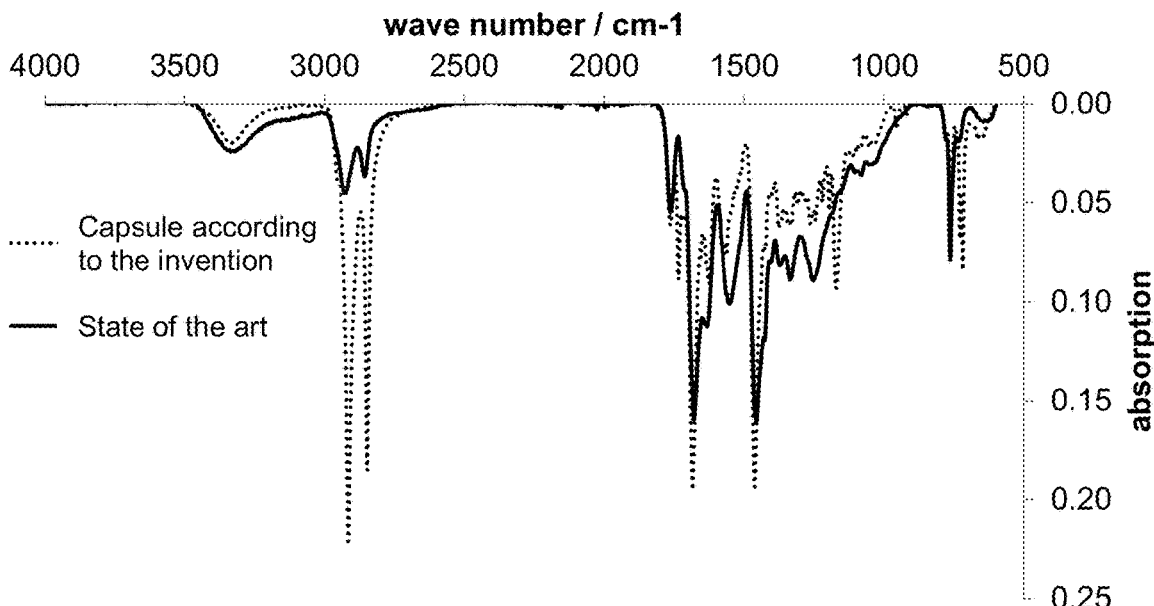
FIG. 3 is a diagram showing the results of an IR spec-troscopic analysis of microcapsules according to the inven-tion and microcapsules of the prior art, i.e. microcapsules based on polyurea/polyurethane structures without release agents. The analysis was carried out using ATR (Attenuated Total Reflection) infrared spectroscopy.

FIG. 3 shows the IR images of the microcapsules according to the invention and of microcapsules of the prior art.

The microcapsules according to the invention were prepared from hexamethylene diisocyanate and 4,4'-methyldiphenylene diisocyanate in a ratio of 75:25. Furthermore, lysine*HCl was used as the first amino acid, glycerol as the hydroxyl group donor and arginine as the second amino acid. DABCO was used as catalyst and a modified starch as protective colloid; beeswax was added as separating agent. The pH of the aqueous phase before the emulsification step and the pH of the emulsion or dispersion at the beginning of the reaction was adjusted to 5.5 in each case. The microcapsules of the prior art were polyurea/polyurethane-based microcapsules without release agent, which were produced at a pH value of 9.

The graph shows clear differences between the bands, especially in the fingerprint area. The vibrations in the range of 700 cm-1 indicate $CH_2$ groups. At 1050 $cm^{-1}$ a clearly more intensive band can be seen compared to the state of the art, which can be attributed to polyurethanes and also polyesters. The polyesters originate on the one hand from the ester bonds of the ocentylsuccinated starch and on the other hand from the ester bonds of the release agent (for example wax). The band at 1170 $cm^{-1}$ can be assigned to a polyester. At 1750 $cm^{-1}$ the vibration indicates a significantly increased proportion of carbonyl carbons. The double vibration in the range from 2500 to 3000 $cm^{-1}$ indicates an increased proportion of carbon chains resulting from the release agent. Furthermore, the comparison of the IR spectra shows that both the microcapsules according to the invention and the microcapsules of the prior art are made of a polyurea/polyurethane polymer.

The process according to the present invention for the production of polyurea/polyurethane microcapsules is advantageously characterised, inter alia, by the fact that the individual crosslinking steps are carried out in a pH-dependent manner.

By optimising the pH value during emulsification and the cross-linking steps of the process according to the invention, microcapsules can be produced with even better performance, i.e. without loss or deterioration in the functionality of the microcapsules, such as olfactory properties and positive secondary properties, such as high stability, namely the ability to retain the active ingredient, than without pH value adjustment. With a targeted pH adjustment, the stability can be improved and thus the free oil content reduced and the sensory performance of the microcapsules increased.

With the process according to the invention, it is possible to deposit alternately defined polyurea- and polyurethane-based crosslinking units or crosslinking matrices around the core comprising the lipophilic active ingredient(s) by interfacial polymerisation, thereby producing the structure of a stable and dense capsule wall or capsule shell. The main components of the capsule shell or capsule wall are basically polyurea or polyurethane cross-linking matrices or crosslinking units. Furthermore, the protective colloid (for example starch) may also be present in the capsule shell or capsule wall via polyurethane linkages. The incorporation of a release agent into the capsule shell or capsule wall further stabilises and densifies the capsule shell or capsule wall.

Furthermore, the process according to the invention is characterised by the fact that protective colloid, amino acids, hydroxyl group donor as main components and polyisocyanates are preferably polymerised and/or cross-linked via specifically catalysed mechanisms and thus enable the production of biobased and biodegradable microcapsules based on biocompatible polymers. Unlike the microcapsules of the prior art, where the polyisocyanates make up a large proportion of the capsule shell material, the exact opposite is the case here: The polyisocyanates no longer function as the main material in the microcapsules according to the invention but serve exclusively as cross-linking agents for the amino acids and the other components mentioned above.

The process according to the invention thus allows to replace part of the polyisocyanate by biodegradable wall materials such as, for example, protective colloid, amino acids, hydroxyl group donor and release agent and thus to reduce the polyisocyanate content without any loss or deterioration in the functionality of the microcapsules, such as, for example, olfactory properties and positive secondary properties such as, for example, high stability, namely the ability to retain the active substance. Thus, the process according to the invention can be used to produce microcapsules which, on the one hand, have excellent functionality and, on the other hand, are readily biodegradable.

Surprisingly, it has been found that the process according to the invention can be used to produce microcapsules with a reduced amount of polyisocyanate by up to 60% without any loss or degradation in the stability of the microcapsules obtained, as shown in the following embodiments. Thus, microcapsules can be produced with a reduced amount of starting substance isocyanate while maintaining the same amount of active ingredient to be encapsulated.

In another aspect, the present invention relates to biodegradable polyurea/polyurethane microcapsules produced according to the process of the invention.

The biodegradable polyurea/polyurethane microcapsules are characterised in that they are composed of or comprise:

(i) a core comprising at least one hydrophobic agent; and (ii) a capsule shell comprising:

a reaction product of a polymerisation and/or cross-linking of at least one polyisocyanate having two or more isocyanate groups, in the presence of at least one protective colloid having at least one first amino acid or an amino acid hydrochloride, a further polymerisation and/or cross-linking with at least one hydroxyl group donor, and a further polymerisation and/or cross-linking with at least one second amino acid; and at least one release agent.

The alternating polymerisation and/or cross-linking of polyisocyanate units with functional amino groups or hydroxyl groups results in a stable capsule wall of alternately defined and dense and thus stable cross-linking matrices or cross-linking units based on polyurethane and polyurea.

In a preferred embodiment, the capsule shell of the biodegradable polyurea/polyurethane microcapsule according to the invention comprises or consists of:

(α) a first crosslinking matrix or first crosslinking units from a polymerisation and/or crosslinking of at least one polyisocyanate having two or more polyisocyanate groups with at least one protective colloid and at least one first amino acid;

(β) a second cross-linking matrix or second cross-linking units from a cross-linking of at least one polyisocyanate having two or more polyisocyanate groups with at least one hydroxyl group donor;

(γ) a third cross-linking matrix or third cross-linking units from a cross-linking of at least one polyisocyanate having two or more polyisocyanate groups with at least one second amino acid; and (δ) at least one release agent; and (ε) optionally a further cross-linking matrix or further polyester-based cross-linking units.

The first cross-linking matrix or cross-linking units of the capsule shell of the microcapsule according to the invention is a polyurea-based network. The second cross-linking matrix or cross-linking units is a polyurethane-based network, and the third cross-linking matrix or cross-linking units is a further polyurea-based network. The fourth cross-linking matrix or units, if any, is a further polyester-based network. The composition of the polyurea and/or polyurethane and/or polyester cross-linking matrices or cross-linking units depends on the polyisocyanate and the cross-linking agent used, i.e. protective colloid, first amino acid, hydroxyl group donor and second amino acid.

In addition to the polyurethane formation and polyurea formation described above, the cross-linking steps described above produce by-products due to the reactivity of the polyisocyanates, for example urea, allophanate, biuret, uretidione, carbodiimide, uretonimine, etc., as described in M. F. Sonnenschein, Introduction to Polyurethane Chemistry, Polyurethanes: Science, Technology, Markets, and Trends, First Ediiton, 2015, John Wiley & Sons, pages 105 to 126, the disclosure of which is incorporated herein by reference in its entirety. These by-products are part of the capsule shell or capsule wall.

Due to the structure of the capsule wall, based on several individual defined and alternating cross-linking matrices or cross-linking units, it is possible to produce particularly stable microcapsules with excellent sensory performance, while at the same time a significant reduction of the shell components is possible. Finally, the stability of the capsule shell is further enhanced by the incorporation of a release agent.

Surprisingly, polyurea/polyurethane fragrance capsules produced according to the method of the invention exhibit higher stability and a reduction in unwanted escaping fragrance oil, as shown in the following embodiments, which can be attributed in particular to more efficient encapsulation of the fragrances.

Surprisingly, it has been found that the process according to the invention can be used to produce microcapsules which, compared to the polyurea/polyurethane microcapsules of the prior art, exhibit a better stability by a factor of at least 1.5, preferably at least 2, as illustrated in the following embodiments.

The microcapsules according to the invention furthermore have a content of free hydrophobic active substance of 0.5% by weight or less, preferably a content of $\leq$0.3% by weight or less, and even more preferably a content of $\leq$0.2% by weight.

Figure 5:
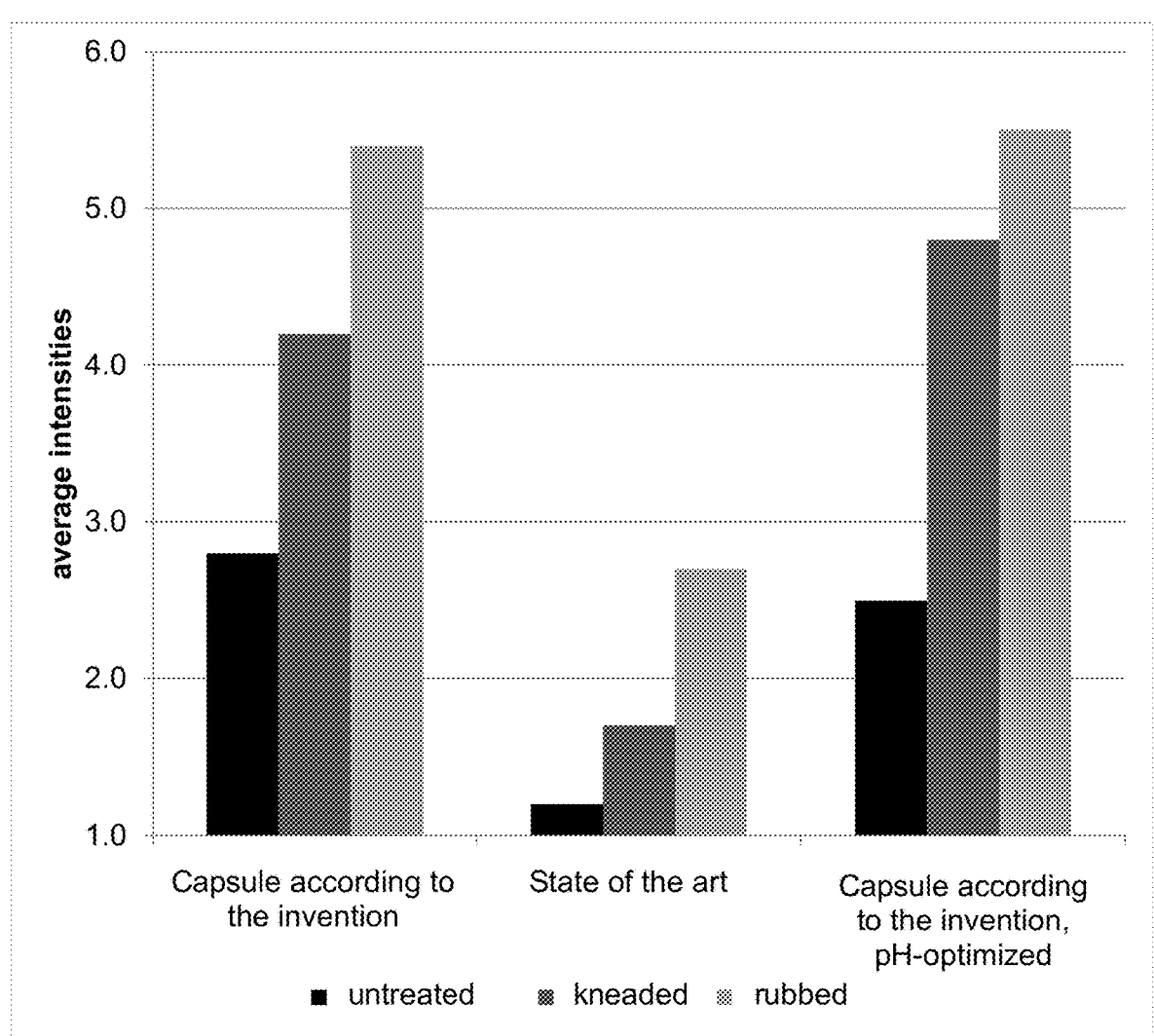
FIG. 5 is a diagram showing the results of a sensory evaluation of microcapsules according to the invention and microcapsules of the prior art, i.e. microcapsules based on polyurea/polyurethane structures without release agents.

The polyurea/polyurethane microcapsules according to the invention also show a significant improvement in sensory performance (fragrance release) compared to prior art capsules, which can be attributed to the stable encapsulation of active ingredient and the associated low active ingredient losses. The microcapsules according to the invention therefore show a significantly higher sensory intensity when fragrance is released by opening the capsules by means of mechanical friction or by pressure, as illustrated in FIG. 5. The polyurea/polyurethane microcapsules according to the invention show a significant improvement in sensory performance (fragrance release) compared to prior art capsules by a factor of at least 1.5, preferably at least 1.75, even more preferably by a factor of at least 2.

Figure 6:
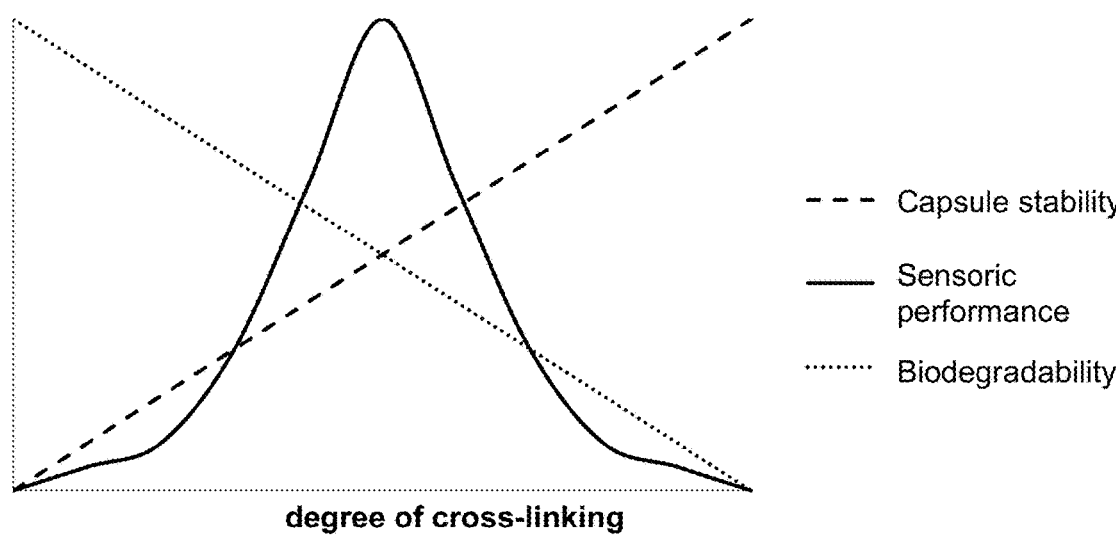
FIG. 6 is a diagram showing the general correlation between microcapsule stability, performance and biodegrad-ability as a function of the degree of cross-linking.

As the degree of cross-linking increases, i.e. as the polyisocyanate content increases, the stability of the microcapsules also increases, but at the same time the ability to biodegrade the capsule shell also decreases, as illustrated in the embodiment examples. FIG. 6 generally shows the correlation between microcapsule stability, performance and biodegradability as a function of the degree of crosslinking. For example, with very stable microcapsules, the performance, for example the sensory performance, is lower, as the number of microcapsules that break open through rubbing, pressure, etc. and release the active ingredients decreases.

The polyurea/polyurethane microcapsules according to the invention have a reduced amount of polyisocyanate by up to 60% compared to prior art polyurea/polyurethane microcapsules, without any loss or degradation in stability or in the loading of the microcapsules with active ingredient to be encapsulated, as shown in the following embodiments. In contrast to the microcapsules of the prior art, the isocyanates no longer function as the main material of the capsule shell or capsule wall but serve exclusively as crosslinkers of the amino acids and the other main components of the capsule shell, such as protective colloid, hydroxyl group donor. The absolute polyisocyanate content of the microcapsules described herein is only 1/60th of the total capsule comprising the active ingredient(s). Assuming that the raw materials react quantitatively, it can be assumed that with 100% wall material, exactly 1/5 of the wall material consists of polyisocyanate and, due to the small amount in which it is represented, this can only be regarded as a cross-linking agent.

Due to the lower polyisocyanate content in the capsule shell or capsule wall on the one hand and the use of a release agent on the other hand, the microcapsules according to the invention are more biodegradable than capsules according to the prior art. Microcapsules according to the invention, which have been produced using a release agent, exhibit significantly better biodegradability, as shown in the following embodiment examples.

Biodegradability is the ability of organic material to be degraded to water, carbon dioxide ($CO_2$) and biomass after a specified time under defined temperature, oxygen and humidity conditions in the presence of microorganisms or fungi.

According to OECD 301F, a microcapsule is considered immediately biodegradable if more than 60% of the wall material has degraded after 28 days.

The microcapsules according to the invention have a biodegradability according to OECD 301 F after 28 days of ≥20%, preferably a biodegradability of ≥50%, even more preferably a biodegradability of ≥70% and most preferably a biodegradability of ≥90%.

The combination of the starting components on the one hand and the sequence of cross-linking on the other hand enable microcapsules according to the invention with sufficient stability (mechanical as well as diffusion-stable in use), high sensory performance and excellent biodegradability at the same time. Thus, the previously valid correlation between sensory performance, high cross-linking and biodegradability could be broken.

Furthermore, the microcapsule according to the invention is a universal capsule with which, according to the present state of the art, a broad spectrum of fragrance compounds or flavourings can be encapsulated, even fragrance compounds or flavourings which have an aldehyde, carboxylic acid or ester functionality, so that there are no restrictions against individual active ingredients.

Due to their advantageous properties, in particular their stability and the targeted release of the active ingredients, the microcapsules according to the invention are suitable for a wide range of applications and in particular for use in household products, textile care products, detergents, fabric softeners, cleaning agents, scent boosters, scent lotions and scent enhancers, cosmetics, personal care products, agricultural products, pharmaceutical products, print coatings for paper and the like.

Therefore, in a further aspect, the present invention relates to the use of the biodegradable polyurea/polyurethane microcapsules according to the invention or a dispersion of the polyurea/polyurethane microcapsules according to the invention (microcapsule slurry) for the manufacture of household products, textile care products, detergents, fabric softeners, cleaning agents, scent boosters, scent lotions or fragrance enhancers in liquid or solid form, cosmetics, personal care products, agricultural products, pharmaceutical products, print coatings for paper and the like.

Finally, the present invention relates to household products, textile care products, detergents, fabric softeners, cleaning agents, scent boosters, scent lotions and scent enhancers, cosmetics, personal care products, agricultural products, pharmaceutical products, print coatings for paper and the like comprising the biodegradable polyurea/polyurethane microcapsules according to the invention or a dispersion of the polyurea/polyurethane microcapsules according to the invention.

EMBODIMENT EXAMPLES

The biodegradable polyurea/polyurethane microcapsules according to the invention and their advantageous properties are described in more detail with reference to the following examples.

Embodiment Example No. 1—Wall Materials in Comparison

TABLE 1

| Component | State of the art/% *) | According to the invention *) |
|---|---|---|
| Isocyanates | 4.8 | 1.7 |
| Protective colloid | 0.3 | 2.2 |
| First amino acid | — | 1.3 |
| Hydroxyl group donor | — | 2.6 |
| Second amino acid/ Basic amine | 1.9 | 0.4 |
| Long chain acid/ alcohols/esters | — | 3.5 |

*) All content data refer to the complete microcapsule including oil.

The microcapsules according to the invention have a significantly lower polyisocyanate content of up to 60%. In contrast to the microcapsules of the prior art, the isocyanates no longer function as the main material and serve exclusively as cross-linking agents for the amino acids and other components of the capsule materials.

Embodiment Example No. 2—Capsule Stability

The following stability data refer to a test at 40° C. in a commercial formulation, such as scent booster or fabric softener.

In the following examples, the capsules chosen as prior art capsules were those whose capsule walls were exclusively due to a polyurea network. In the production of these capsules, generally no catalyst was used, and the synthesis was carried out at a pH of 9. Polyvinyl alcohol was used as the protective colloid.

The free oils were determined by letting the slurry stand in isopropanol for 30 seconds. The oil content was then determined by SPME followed by GC/MS.

Example 1—Capsule Stability with and without pH Optimisation

The behaviour of the free oils was determined by varying the pH. Microcapsules according to the invention were prepared by using an isocyanate mixture consisting of hexamethylene diisocyanate and 4,4'-methyldiphenylene diisocyanate in a ratio of 75:25. Furthermore, lysine*HCl was used as the first amino acid, glycerol as the hydroxyl group donor and arginine as the second amino acid. DABCO was used as catalyst and a modified starch as protective colloid. The starch used was in the form of a succinate. Beeswax was used as the wax. TomCap was used as the phase to be encapsulated. The non-optimised pH value that the emulsion or dispersion has at the beginning of the respective reaction was 8.5 and the optimised pH value that the emulsion or dispersion has at the beginning of the respective reaction was 5.5.

TABLE 2

| pH value | Stability/% (4 weeks Scent Booster at 40° C.) |
|---|---|
| pH value = 8.5 (not optimised) | 25 |
| pH value = 5.5 (pH value optimised) | 47 |

Obviously, at a slightly acidic pH, the stability of the microcapsules is significantly improved. The capsules are considered stable at a free oil of <1%. The lower the free oil content, the more stable the capsule.

Example 2—Capsule Stability as a Function of pH Value

The behaviour of the free oils was determined by varying the pH. Microcapsules according to the invention were prepared by using an isocyanate mixture consisting of hexamethylene diisocyanate and 4,4'-methyl diphenylene diisocyanate in a ratio of 75:25. Furthermore, lysine*HCl was used as the first amino acid, glycerol as the hydroxyl group donor and histidine as the second amino acid. DABCO was used as catalyst and a modified starch as protective colloid. The starch used was in the form of a succinate. Beeswax was used as the wax. TomCap was used as the phase to be encapsulated.

TABLE 3

| pH value | Stability/% | |
|---|---|---|
| | 1 week 40° C. Softener | 4 weeks 40° C. Softener |
| 2 | — | — |
| 3 | 22 | — |
| 4 | 43 | 33 |
| 5 | 56 | 47 |
| 6 | 57 | 43 |
| 7 | — | — |

TABLE 3-continued

| pH value | Stability/% | |
|---|---|---|
| | 1 week 40° C. Softener | 4 weeks 40° C. Softener |
| 8 | 21 | — |
| 9 | 25 | — |
| 10 | 28 | — |
| 11 | — | — |

The optimum pH value of the emulsion or dispersion at the beginning of the respective reactions in the process according to the invention is in the range of 4 to 7 in order to produce stable microcapsules.

Example 3—Capsule Stability as a Function of Polyisocyanate Composition (Comparison of Single Polyisocyanate and Combination of Two Different Polyisocyanates)

Microcapsules according to the invention were prepared using different single polyisocyanates or a combination of two different polyisocyanates, guanidinium carbonate, polyvinyl alcohol as protective colloid with TomCap as perfume oil:

TABLE 4

| Isocyanates | Stability/% | | |
|---|---|---|---|
| | Free oil/% | 3 days 50° C. in fabric softener | 10 days 50° C. in fabric softener |
| Hexamethylene diisocyanate/ 4,4'Diphenylmethane diisocyanate 80:20 | 0.068 | 80 | 74 |
| Hexamethylene diisocyanate | 0.065 | 43 | 32 |
| Pentamethylene diisocyanate | 0.113 | 72 | 62 |
| 4,4'Diphenylmethane diisocyanate | 0.111 | 78 | 69 |

The use of a combination of two different isocyanates resulted in microcapsules that exceed the stability of the single isocyanate systems. This makes the use of a mixture of two different isocyanates preferable.

Example 4—Capsule Stability as a Function of Polyisocyanate Composition (Comparison of Aliphatic-Aliphatic Polyisocyanate Mixture and Aliphatic-Aromatic Polyisocyanate Mixture)

Microcapsules according to the invention were prepared using an aliphatic-aliphatic polyisocyanate mixture and an aliphatic-aromatic polyisocyanate mixture as follows:

Aliphatic-aliphatic polyisocyanate mixture: pentamethylene diisocyanate and hexamethylene diisocyanate in a ratio of 50:50.

Aliphatic-aromatic isocyanate mixture: hexamethylene diisocyanate and 4,4'-methyl-diphenylene diisocyanate in a ratio of 75:25.

Furthermore, lysine*HCl was used as the first amino acid, glycerol as the hydroxyl group donor and arginine as the second amino acid. DABCO was used as catalyst and a modified starch as protective colloid. TomCap was used as the phase to be encapsulated. Beeswax was used as the wax. The starch used is in the form of a succinate.

TABLE 5

| Isocyanate mixture | Free oil/% |
|---|---|
| aliphatic-aliphatic | 0.49 |
| aliphatic-aromatic | 0.09 |

The free oils in both samples are well below 1%, which means that both capsules are considered stable. The microcapsule made of an aliphatic-aliphatic polyisocyanate mixture is just as stable as a microcapsule made of an aliphatic-aromatic polyisocyanate mixture.

Example 5—Capsule Stability with and without Further Catalyst

Microcapsules according to the invention were prepared using an isocyanate mixture consisting of hexamethylene diisocyanate and 4,4'-methyldiphenylene diisocyanate in a ratio of 75:25. Furthermore, lysine*HCl was used as the first amino acid, glycerol as the hydroxyl group donor and histidine as the second amino acid. DABCO was used as catalyst and a modified starch as protective colloid. The starch used was in the form of a succinate. Beeswax was used as the wax. TomCap was used as the phase to be encapsulated. In addition, another catalyst was used in the production.

TABLE 6

| Para-toluenesulfonic acid | Stability/% | |
|---|---|---|
| | 1 week 40° C. Softener | 4 weeks 40° C. Softener |
| With | 52 | 49 |
| Without | 32 | 24 |

The microcapsules produced using another catalyst are twice as stable after four weeks as microcapsules produced without using another catalyst.

Example 6—Capsule Stability with and without First Catalyst

Microcapsules according to the invention were prepared using an isocyanate mixture consisting of hexamethylene diisocyanate and 4,4'-methyldiphenylene diisocyanate in a ratio of 75:25. Furthermore, lysine*HCl was used as the first amino acid, glycerol as the hydroxyl group donor and histidine as the second amino acid. Para-toluenesulfonic acid was used as a further or second catalyst and a modified starch as a protective colloid. The starch used was in the form of a succinate. Beeswax was used as wax. TomCap was used as the phase to be encapsulated.

TABLE 7

| DABCO | Stability/% | |
|---|---|---|
| | 1 week 40° C. Softener | 4 weeks 40° C. Softener |
| With | 54 | 46 |
| Without | 7 | — |

The microcapsules produced using a first catalyst are much more stable, which is why the use of a polyurethane catalyst, such as DABCO, is essential.

Embodiment Example No. 3—Biodegradability and Free Oil in Relation to the Amount of Cross-Linker (Isocyanates)

The free oil content was determined as described above. Biodegradability according to OECD 301F was determined as follows: Degradability of the wall material in a non-preadapted inoculum, measured by manometric respiration (oxygen consumption).

TABLE 7

| Crosslinker quantity/% | Free oil/% | Biodegradability/% according to OECD 301F within 28 days |
|---|---|---|
| 4.3 | 0.13 | 30 |
| 3.2 | 0.22 | 42 |
| 2.0 | 0.71 | 96 |

The biodegradability increases when the amount of polyisocyanate (cross-linker) decreases. Surprising in this case is the very small increase in free oil, which means that the capsules can be assumed to be stable.

Embodiment Example No. 4—Comparison of Biodegradability with and without Release Agent

TABLE 8

| Component | Microcapsule without release agent/% *) | Microcapsule with release agent/% *) |
|---|---|---|
| Isocyanates | 1.8 | 1.7 |
| Protective colloid | 2.2 | 2.2 |
| Amino acid | 1.4 | 1.3 |
| Hydroxyl group donor | 2.7 | 2.6 |
| Amino acid | 1.8 | 1.7 |
| Release agent | — | 3.5 |
| Biodegradability | 6.7% | 96% |
| Capsule wall material | according to OECD 301F within 28 days | according to OECD 301F within 28 days |

*) All content data refer to the complete microcapsule including oil
*) Content data related to capsule including oil The capsules according to the invention show that there is a biodegradability of 96%, which means that the wall material can be assumed to be immediately biodegradable.

Embodiment Example No. 6—Comparison of Biodegradability in Relation to Sodium Sulphate and Toxicity Control The microcapsules of embodiment no. 5 according to the invention were used to test the biodegradability of the wall material in accordance with OECD 301 F. For this purpose, sodium benzoate was used as process control and a mixture of the microcapsules according to the invention and sodium benzoate as toxicity control.

Test replicate 1 and 2=capsule according to the invention

Procedure control replicate 1 and 2=sodium sulphate

Toxicity control=combination of capsule according to the invention and sodium sulphate in order to control the toxicological effect.

Figure 4:
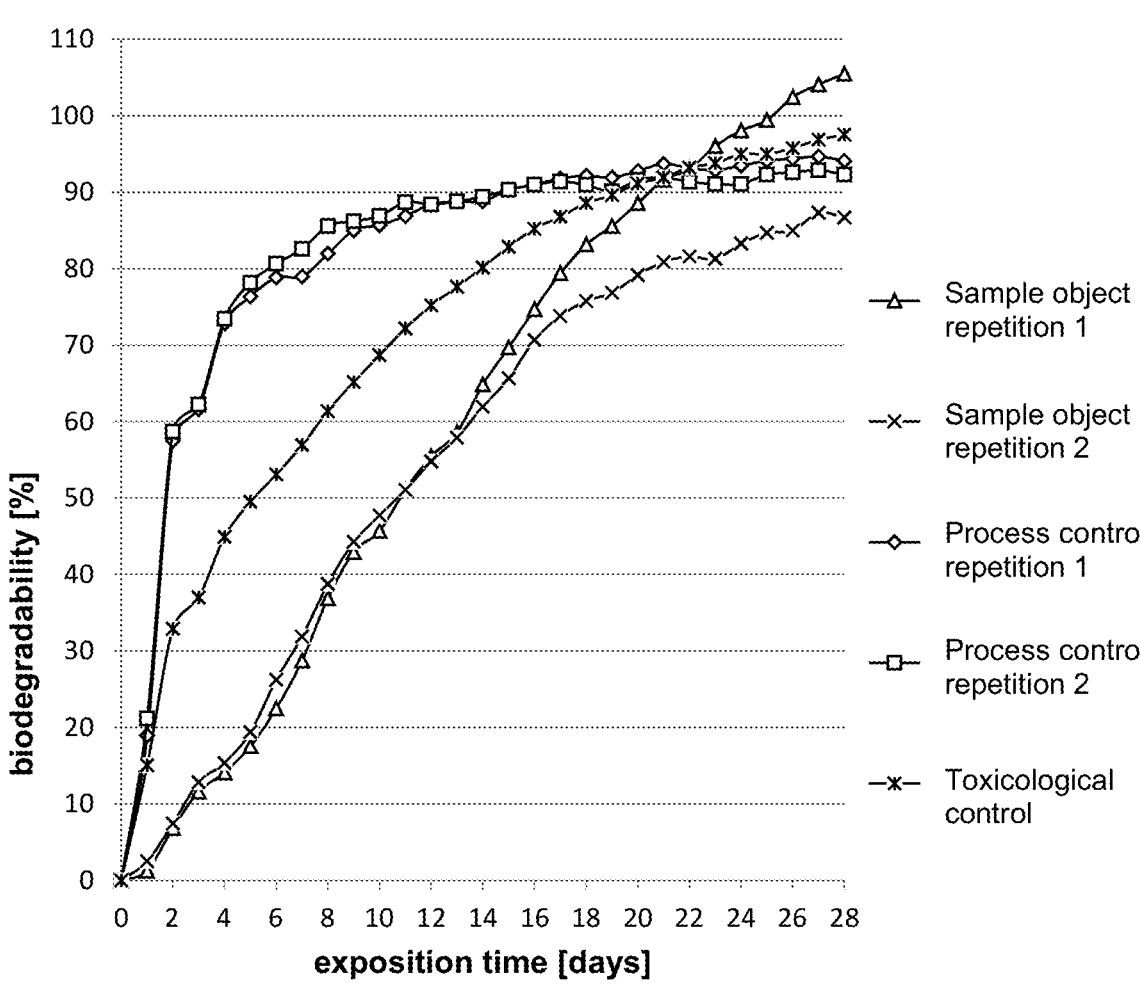
FIG. 4 is a diagram showing the biodegradability of microcapsules according to OECD 301 F in comparison with sodium benzoate and a toxicity control (mixture of microcapsules according to the invention and sodium ben-zoate).

The test results are shown in FIG. 4.

The capsules according to the invention show that there is a biodegradability of 96% on average of two samples, which means that the wall material can be assumed to be immediately biodegradable. The toxicity control also shows degradability, proving that the wall material of the capsule according to the invention is not persistent.

Embodiment Example No. 7—Comparison of Biodegradability with and without Wax Microcapsules according to the invention were prepared by using an isocyanate mixture consisting of hexamethylene diisocyanate and 4,4'-methyldiphenylene diisocyanate in a ratio of 75:25. Furthermore, lysine*HCl was used as the first amino acid, glycerol as the hydroxyl group donor and arginine as the second amino acid. DABCO was used as catalyst and a modified starch as protective colloid. Subsequently, the wall material was separated by using a centrifuge, a rotary evaporator and a vacuum drying oven. Ethyl acetate was used as the phase to be encapsulated. The waxes used are given in the table below. The starch used is in the form of a succinate.

TABLE 9

| Waxes | Biodegradability according to OECD 301 F after 28 days/%. |
| --- | --- |
| No wax | 12 |
| Beeswax | 96 |
| Sunflower seed wax | 72 |

According to OECD 301F, both capsules are considered biodegradable due to the use of the wax. The use of the waxes is surprising in that, despite the small amount of wax, the biodegradability increases disproportionately.

Embodiment Example No. 8—Sensory Test

For the sensory evaluation, the microcapsules according to the invention were compared with microcapsules from the prior art, i.e. microcapsules based on polyurea/polyurethane structures without release agents and a pH value of 9.

The microcapsules according to the invention were prepared from hexamethylene diisocyanate and 4,4'-methyldiphenylene diisocyanate in a ratio of 75:25. Furthermore, lysine*HCl was used as the first amino acid, glycerol as the hydroxyl group donor and arginine as the second amino acid. DABCO was used as catalyst and a modified starch as protective colloid; beeswax was added as a separating agent. The pH value that the emulsion or dispersion had at the beginning of the respective reactions was adjusted to pH 5.5.

The sensory evaluation was carried out as follows: The above microcapsules were each added to a fabric softener with an oil concentration of 0.2 wt. % and then washed. Smelling was done on mixed fibre cloths made of cotton and polyester.

12 test persons rated the scent intensity of mixed fibre cloths after washing on a scale from 1 (no scent) to 9 (very strong scent). The scent rating was done in three steps. The first step describes the smelling of an untreated cloth. The second step describes the smelling of a lightly kneaded cloth; for this purpose, the cloth was subjected to slight mechanical stress by moving it back and forth between the hands several times, causing the capsules to break. The third step describes the smelling after the cloths were rubbed strongly and thus the capsules broke.

The microcapsules according to the invention have a significantly better performance, as illustrated in FIG. 5. This can be attributed to the specific modification of the system: through the pH-value-optimised cross-linking and the use of a separating agent, a stable, whereby the capsules smell better, but nevertheless biodegradable capsule wall structure is formed.

The invention claimed is:

1. Process for preparing a biodegradable polyurea/polyurethane microcapsule comprising the following steps in this order:

(a) carrying out a first polymerisation and/or cross-linking step comprising:

(a1) providing an internal non-aqueous phase comprising at least one polyisocyanate having two or more isocyanate groups and at least one lipophilic active substance to be encapsulated;

(a2) providing an external aqueous phase comprising at least one protective colloid and optionally an emulsifier, and adjusting the pH of the external aqueous phase to a pH of from 1 to 5;

(a3) mixing the internal non-aqueous phase and the external aqueous phase to obtain an oil-in-water emulsion or dispersion; and (a4) adding at least one first amino acid or amino acid hydrochloride and a catalyst and adjusting the pH of the resulting emulsion or dispersion to a pH of 4 to 8;

(b) carrying out a second polymerisation and/or cross-linking step by adding at least one hydroxyl group donor;

(c) carrying out a third polymerisation and/or crosslinking step by adding at least one second amino acid and adjusting the pH of the emulsion or dispersion to a pH of 4 to 8, to obtain a microcapsule dispersion;

(d) optionally adding a further catalyst and adjusting the pH of the resulting microcapsule dispersion to a pH of 4 to 7;

(e) curing the microcapsule dispersion obtained from step (c) or (d) at a temperature of at least 60° C. for a period of at least 60 minutes;

(f) adding at least one release agent and incorporating the release agent into the shell of the microcapsule;

(g) post-curing the microcapsules obtained in step (f); and optionally:

(h) separating the microcapsules from the microcapsule dispersion and, if necessary, drying the microcapsules or adjusting the viscosity of the slurry comprising the microcapsules by adding a thickening agent.

2. Process according to claim 1, wherein the at least one polyisocyanate having two or more isocyanate groups is selected from the group consisting of aliphatic, cycloaliphatic, hydroaromatic, aromatic and heterocyclic polyisocyanates, their substitution products, and mixtures of the aforementioned compounds.

3. Process according to claim 1, wherein the at least one lipophilic active substance to be encapsulated is selected from the group consisting of fragrance compounds, flavourings, cooling agents, TRPV1 and TRPV3 modulators, substances which cause a pungent taste or a warmth or heat sensation on the skin or mucous membranes or a tingling sensation in the mouth or throat, active substances with a pungent or acrid or astringent effect, pesticides, biocides, insecticides, repellents, food additives, cosmetic active ingredients, pharmaceutical active ingredients, dyes, dye precursors, fluorescent dyes, agrochemicals, optical brighteners, solvents, waxes, silicone oils, lubricants, print coatings for paper, and mixtures of two or more of the above-mentioned active ingredients;

wherein the substances which cause a pungent taste or a warmth or heat sensation on the skin or mucous membranes are selected from the group consisting of paprika powder, chilli pepper powder, extracts of paprika, extracts of pepper, extracts of chilli pepper, extracts of ginger roots, extracts of grains of paradise, extracts of para cress, extracts of Japanese pepper, extracts of Kaempferia galanga, extracts of Alpinia galanga, extracts of water pepper, capsaicinoids; gingerols; shogaols; gingerdiones; paradoles; dehydrogingerdiones; piperine; piperine derivatives; ethyl 2-(4-hydroxy-3-methoxy-phenyl)acetate and 3-phenylpropyl 2-(4-hydroxy-3-methoxy-phenyl)acetate and mixtures thereof;

wherein the substances which cause a tingling sensation in the mouth or throat are selected from the group consisting of 2E,4E-decadienoic acid-N-isobutylamide; 2E,4Z-decadienoic acid-N-isobutylamide; 2Z,4Z-decadienoic acid-N-isobutylamide; 2Z,4E-decadienoic acid-N-isobutylamide; 2E,4E-decadienoic acid-N-([2S]-2-methylbutyl)amide; 2E,4E-decadienoic acid-N-([2S]-2-methylbutyl)amide; 2E,4E-decadienoic acid-N-([2R]-2-methylbutylamide); 2E,4Z-decadienoic acid-N-(2-methylbutyl)amide; 2E,4E-decadienoic acid-N-piperide; 2E-decenoic acid-N-isobutylamide; 3E-decenoic acid-N-isobutylamide; 3E-nonenoic acid-N-isobutylamide; 2E,6Z,8E-decatrienoic acid-N-isobutylamide; 2E,6Z,8E-decatrienoic acid-N-([2S]-2-methylbutyl)amide; 2E,6Z,8E-decatrienoic acid-N-([2R]-2-methylbutyl)amide; 2E-decen-4-ynoic acid-N-isobutylamide; 2Z-decen-4-ynoic acid-N-isobutylamide; 2E,6Z,8E, 10E-dodecatetraenoic acid-N-(2-methylpropyl)amide; 2E,6Z,8E, 10E-dodecatetraenoic acid-N-(2-hydroxy-2-methylpropyl) amide; 2E,6E,8E, 10E-dodecatetraenoic acid-N-(2-hydroxy-2-methylpropyl)amide; 2E,4E,8Z,10E,12E-tetradecapentaenoic acid-N-(2-hydroxy-2-methylpropyl)amide; 2E,4E,8E,10E,12E-tetradecapentaenoic acid-N-(2-hydroxy-2-methylpropyl)amide; 2E,4E,8Z,10E,12E-tetradecapentaenoic acid-N-(2-methyl-2-propenyl)amide; 2E,4E,8Z, 10E, 12E-tetradecapentaenoic acid-N-(2-methylpropyl)amide; 2E,4E,8Z, 11Z-tetradecatetraenoic acid-N-(2-hydroxy-2-methylpropyl)amide; 2E,4E,8Z, 11E-tetradecatetraenoic acid-N-(2-hydroxy-2-methylpropyl)amide; 2E,4E,8Z-tetradecatrienoic acid-N-(2-hydroxy-2-methylpropyl)amide and 2E,4E-tetradecadienoic acid-N-(2-hydroxy-2-methylpropyl) amide and mixtures thereof;

wherein the active substances with a pungent or acrid effect are selected from the group consisting of aromatic isothiocyanates, allyl isothiocyanate, cyclopropyl isothiocyanate, butyl isothiocyanate, 3-methylthiopropyl isothiocyanate and mixtures thereof, and wherein the active substances with astringent effect are selected from the group consisting of: catechins, their oligomers and their C- and O-glycosides; dihydroflavonoids and their C- and O-glycosides, flavonols and their C- and O-glycosides, and mixtures thereof.

4. Process according to claim 1, wherein the at least one lipophilic active ingredient to be encapsulated is selected from the group consisting of fragrance compounds and flavourings having aldehyde, carboxylic acid or ester functionality.

5. Process according to claim 1, wherein the protective colloid is selected from the group consisting of
   diols;
   polyols;

polyvinylpyrrolidone, maleic acid vinyl copolymers, sodium lignosulphonates, maleic anhydride/styrene copolymers, ethylene/maleic anhydride copolymers, copolymers of ethylene oxide, propylene oxide and acid esters of polyethoxylated sorbitol, sodium dodecyl sulphate;
   animal and vegetable polymers;
   and mixtures of the aforementioned compounds.

6. Process according to claim 1, wherein the protective colloid is used in combination with starch.

7. Process according to claim 1, wherein the at least one first amino acid or amino acid hydrochloride is selected from the group consisting of arginine, histidine, lysine, tryptophan, ornithine, arginine hydrochloride, histidine hydrochloride, lysine hydrochloride, tryptophan hydrochloride, ornithine hydrochloride, and mixtures thereof.

8. Process according to claim 1, wherein the catalyst added in step (a4) is selected from the group consisting of diazobicyclo[2.2.2]octane (DABCO), bismuth catalyst, tin catalyst, and mixtures of the aforementioned catalysts; and the optionally further catalyst is selected from the group consisting of para-toluenesulfonic acid, sulfuric acid, germanium oxide and enzymatic catalysts.

9. Process according to claim 1, wherein the hydroxyl group donor is a polyol having two or more hydroxyl functional groups.

10. Process according to claim 1, wherein the at least one second amino acid is selected from the group consisting of arginine, histidine, aspartic acid, lysine, glycine, alanine, proline, cysteine, glutamine, leucine, serine, tryptophan, valine, threonine, ornithine, and mixtures thereof.

11. Process according to claim 1, wherein the at least one release agent is selected from the group consisting of
   long-chain, aliphatic, linear or branched, saturated or unsaturated carboxylic acids with 12 to 30 C atoms;
   long-chain, aliphatic, linear or branched, saturated or unsaturated primary alcohols with 12 to 30 C atoms;
   esters of long-chain, aliphatic saturated carboxylic acids having 12 to 30 C atoms with long-chain, aliphatic primary alcohols having 12 to 30 C atoms;
   and mixtures of the aforementioned release agents.

12. Biodegradable polyurea/polyurethane microcapsule comprising:
   (i) a core comprising at least one hydrophobic agent; and
   (ii) a capsule shell comprising:
      a reaction product of a polymerisation and/or cross-linking of at least one polyisocyanate having two or more isocyanate groups, in the presence of a protective colloid with at least one first amino acid or amino acid hydrochloride, a second polymerisation and/or cross-linking with at least one hydroxyl group donor, and a third polymerisation and/or cross-linking with at least one second amino acid;
      at least one release agent; and
      a further polyester-based cross-linking matrix or further polyester-based cross-linking units from the reaction of protective colloid, hydroxyl group donor and release agent,
   wherein the protective colloid is selected from the group consisting of diols, polyols, polyvinylpyrrolidone, maleic acid vinyl copolymers, sodium lignosulphonates, maleic anhydride/styrene copolymers, ethylene/maleic anhydride copolymers, copolymers of ethylene oxide, propylene oxide and acid esters of polyethoxylated sorbitol, sodium dodecyl sulphate, animal and vegetable polymers, and mixtures of the aforementioned compounds;

the hydroxyl group donor is a polyol having two or more hydroxyl functional groups, and the release agent is selected from the group consisting of long-chain, aliphatic, linear of branched, saturated or unsaturated carboxylic acids with 12 to 30° C. atoms, long-chain, aliphatic, linear or branched, saturated or unsaturated primary alcohols with 12 to 30 C atoms, esters of long-chain, aliphatic saturated carboxylic acids having 12 to 30 C atoms with long-chain, aliphatic primary alcohols having 12 to 30° C. atoms and mixtures of the aforementioned release agents.

13. Biodegradable polyurea/polyurethane microcapsule according to claim 12, wherein the capsule shell comprises:

(a) a first crosslinking matrix or first crosslinking units from a polymerisation and/or crosslinking of at least one polyisocyanate having two or more polyisocyanate groups with at least one protective colloid and at least one first amino acid;

(b) a second crosslinking matrix or second crosslinking units from a crosslinking of at least one polyisocyanate having two or more polyisocyanate groups with at least one hydroxyl group donor;

(c) a third crosslinking matrix or third crosslinking units from a crosslinking of at least one polyisocyanate having two or more polyisocyanate groups with at least one second amino acid; and (d) at least one release agent; and (e) a further polyester-based cross-linking matrix or further polyester-based cross-linking units.

14. Biodegradable polyurea/polyurethane microcapsule according to claim 12, which has a biodegradability according to OECD 301 F after 28 days of ≥20% and/or has a free hydrophobic active ingredient content of ≤0.3 wt.-%.

15. A method of manufacturing a product comprising incorporating the biodegradable polyurea/polyurethane microcapsule according to claim 12 into the product, wherein the product is a household product, textile care product, detergent, fabric softener, cleaning agent, scent booster, scent lotion, scent enhancer in liquid or solid form, cosmetic, personal care product, perfume composition, agricultural product, pharmaceutical product or print coating for paper.

16. A household product, textile care product, detergent, fabric softener, cleaning agent, scent booster, scent lotion, scent enhancer, cosmetic, personal care product, perfume composition, agricultural product, pharmaceutical product or print coating for paper comprising the biodegradable polyurea/polyurethane microcapsule according to claim 12.

17. Process according to claim 2, wherein the at least one lipophilic active substance to be encapsulated is selected from the group consisting of fragrance compounds, flavourings, cooling agents, TRPV1 and TRPV3 modulators, substances which cause a pungent taste or a warmth or heat sensation on the skin or mucous membranes or a tingling sensation in the mouth or throat, active substances with a pungent or acrid or astringent effect, pesticides, biocides, insecticides, repellents, food additives, cosmetic active ingredients, pharmaceutical active ingredients, dyes, dye precursors, fluorescent dyes, agrochemicals, optical brighteners, solvents, waxes, silicone oils, lubricants, print coatings for paper, and mixtures of two or more of the above-mentioned active ingredients;

wherein the substances which cause a pungent taste or a warmth or heat sensation on the skin or mucous membranes are selected from the group consisting of: paprika powder, chilli pepper powder, extracts of paprika, extracts of pepper, extracts of chilli pepper, extracts of ginger roots, extracts of grains of paradise, extracts of para cress, extracts of Japanese pepper, extracts of Kaempferia galanga, extracts of Alpinia galanga, extracts of water pepper, capsaicinoids; gingerols; shogaols; gingerdiones; paradoles; dehydrogingerdiones; piperine; piperine derivatives; ethyl 2-(4-hydroxy-3-methoxy-phenyl)acetate and 3-phenylpropyl 2-(4-hydroxy-3-methoxy-phenyl) acetate and mixtures thereof;

wherein the substances which cause a tingling sensation in the mouth or throat are selected from the group consisting of 2E,4E-decadienoic acid-N-isobutylamide; 2E,4Z-decadienoic acid-N-isobutylamide; 2Z,4Z-decadienoic acid-N-isobutylamide; 2Z,4E-decadienoic acid-N-isobutylamide; 2E,4E-decadienoic acid-N-([2S]-2-methylbutyl)amide; 2E,4E-decadienoic acid-N-([2S]-2-methylbutyl)amide; 2E,4E-decadienoic acid-N-([2R]-2-methylbutylamide); 2E,4Z-decadienoic acid-N-(2-methylbutyl)amide; 2E,4E-decadienoic acid-N-piperide; 2E-decenoic acid-N-isobutylamide; 3E-decenoic acid-N-isobutylamide; 3E-nonenoic acid-N-isobutylamide; 2E,6Z,8E-decatrienoic acid-N-isobutylamide; 2E,6Z,8E-decatrienoic acid-N-([2S]-2-methylbutyl)amide; 2E,6Z,8E-decatrienoic acid-N-([2R]-2-methylbutyl)amide; 2E-decen-4-ynoic acid-N-isobutylamide; 2Z-decen-4-ynoic acid-N-isobutylamide; 2E,6Z,8E, 10E-dodecatetraenoic acid-N-(2-methylpropyl)amide; 2E,6Z,8E, 10E-dodecatetraenoic acid-N-(2-hydroxy-2-methylpropyl) amide; 2E,6E,8E, 10E-dodecatetraenoic acid-N-(2-hydroxy-2-methylpropyl)amide; 2E,4E,8Z,10E,12E-tetradecapentaenoic acid-N-(2-hydroxy-2-methylpropyl)amide; 2E,4E,8E,10E,12E-tetradecapentaenoic acid-N-(2-hydroxy-2-methylpropyl)amide; 2E,4E,8Z,10E,12E-tetradecapentaenoic acid-N-(2-methyl-2-propenyl) amide; 2E,4E,8Z,10E, 12E-tetradecapentaenoic acid-N-(2-methylpropyl)amide; 2E,4E,8Z,11Z-tetradecatetraenoic acid-N-(2-hydroxy-2-methylpropyl)amide; 2E,4E,8Z,11E-tetradecatetraenoic acid-N-(2-hydroxy-2-methylpropyl)amide; 2E,4E,8Z-tetradecatrienoic acid-N-(2-hydroxy-2-methylpropyl)amide and 2E,4E-tetradecadienoic acid-N-(2-hydroxy-2-methylpropyl) amide and mixtures thereof;

wherein the active substances with a pungent or acrid effect are selected from the group consisting of aromatic isothiocyanates, allyl isothiocyanate, cyclopropyl isothiocyanate, butyl isothiocyanate, 3-methylthiopropyl isothiocyanate and mixtures thereof; and wherein the active substances with astringent effect are selected from the group consisting of: catechins, their oligomers and their C- and O-glycosides; dihydroflavonoids and their C- and O-glycosides, flavonols and their C- and O-glycosides, and mixtures thereof.

18. Process according to claim 2, wherein the at least one lipophilic active ingredient to be encapsulated is selected from the group consisting of fragrance compounds and flavourings having aldehyde, carboxylic acid or ester functionality.

19. Process according to claim 5, wherein the protective colloid is used in combination with starch.

20. Process according to claim 5, wherein the at least one first amino acid or amino acid hydrochloride is selected from the group consisting of arginine, histidine, lysine, tryptophan, ornithine, arginine hydrochloride, histidine hydrochloride, lysine hydrochloride, tryptophan hydrochloride, orni-thine hydrochloride, and mixtures thereof.

\* \* \* \* \*